US012637683B2

(12) United States Patent
Huang et al.

(10) Patent No.: US 12,637,683 B2
(45) Date of Patent: May 26, 2026

(54) *CINNAMOMUM BURMANNII* MONOTERPENE SYNTHASE CBTPS1, RELATED BIOMATERIAL THEREOF AND APPLICATION THEREOF

(71) Applicant: Sichuan Honghe Biotechnology Co., Ltd., Nanchong Sichuan (CN)

(72) Inventors: Luqi Huang, Beijing (CN); Ping Su, Beijing (CN); Rui Ma, Beijing (CN); Guanghong Cui, Beijing (CN); Juan Guo, Beijing (CN); Baolong Jin, Beijing (CN); Yating Hu, Beijing (CN); Jichen Bao, Beijing (CN)

(73) Assignee: Sichuan Honghe Biotechnology Co., Ltd. (CN)

( * ) Notice: Subject to any disclaimer, the term of this patent is extended or adjusted under 35 U.S.C. 154(b) by 122 days.

(21) Appl. No.: 17/774,705

(22) PCT Filed: Nov. 5, 2020

(86) PCT No.: PCT/CN2020/126683
§ 371 (c)(1),
(2) Date: May 5, 2022

(87) PCT Pub. No.: WO2021/088914
PCT Pub. Date: May 14, 2021

(65) Prior Publication Data
US 2022/0396802 A1      Dec. 15, 2022

(30) Foreign Application Priority Data
Nov. 7, 2019      (CN) ......................... 201911082325.8

(51) Int. Cl.
*C12N 15/81*      (2006.01)
*C12N 9/88*      (2006.01)
(Continued)

(52) U.S. Cl.
CPC ............... *C12N 15/81* (2013.01); *C12N 9/88* (2013.01); *C12N 15/70* (2013.01); *C12N 15/82* (2013.01); *C12P 5/007* (2013.01); *C12P 7/02* (2013.01)

(58) Field of Classification Search
None
See application file for complete search history.

(56) References Cited

U.S. PATENT DOCUMENTS

2011/0160501 A1*    6/2011    Martin ..................... C12N 9/88
585/16
2017/0253885 A1      9/2017    Jang et al.

FOREIGN PATENT DOCUMENTS

CN          105002194 A        10/2015
CN          107002062 A        8/2017
(Continued)

OTHER PUBLICATIONS

Chaw et al., UniProt Database, Acc. No. A0A3S3NMD7. "Stout camphor tree genome fills gaps in understanding of flowering plant genome evolution." Nature Plants, 2019; 5:63-73. (Year: 2019).*
(Continued)

*Primary Examiner* — Amjad Abraham
*Assistant Examiner* — Dequantarius Javon Speed
(74) *Attorney, Agent, or Firm* — Lerner David LLP

(57) ABSTRACT

Provided are a *Cinnamomum burmannii* monoterpene synthase CbTPS1, an amino acid sequence thereof, a nucleic acid molecule encoding the protein, an use thereof in preparing the monoterpene synthase, and a method for preparing dextrorotatory borneol by using the *Cinnamomum burmannii* monoterpene synthase CbTPS1.

5 Claims, 3 Drawing Sheets
Specification includes a Sequence Listing.

(51) Int. Cl.

| | | |
|---|---|---|
| *C12N 15/70* | (2006.01) | |
| *C12N 15/82* | (2006.01) | |
| *C12P 5/00* | (2006.01) | |
| *C12P 7/02* | (2006.01) | |

(56) References Cited

FOREIGN PATENT DOCUMENTS

| | | |
|---|---|---|
| CN | 107630025 A | 1/2018 |
| CN | 108395997 A | 8/2018 |
| CN | 108893482 A | 11/2018 |
| WO | 0107565 A2 | 2/2001 |
| WO | 2012058636 A1 | 5/2012 |

OTHER PUBLICATIONS

Degenhardt, J., Köllner, T. G., & Gershenzon, J. (2009). Monoterpene and sesquiterpene synthases and the origin of terpene skeletal diversity in plants. Phytochemistry, 70(15-16), 1621-1637. (Year: 2009).*

Plumeriastuti, H., & Effendi, M. H. (2019). Identification of bioactive compound of the essential oils of Cinnamomum burmannii from several areas in Indonesia by gas chromatography-mass spectrometry method for antidiabetic potential. Natl Jour of Physiology, Pharmacy and Pharmacology, 9(4), 279-283. (Year: 2019).*

Monica Borghi et al. "Cloning and characterization of a monoterpene synthase gene from flowers of *Camelina sativa*" Planta, vol. 247, Jan. 15, 2018 (Jan. 15, 2018), ISSN: 0032-0935, pp. 443-457.

Yang, T. et al. "Cinnamomum tenuipilum mRNA for geraniol synthase (GerS gene)" GenBank, Accession No. AJ457070, Apr. 15, 2005 (Apr. 15, 2005). 2 pgs.

International Search Report for PCT/CN2020/126683 dated Feb. 8, 2021. 6 pgs.

Extended European Search Report including Written Opinion for Application No. 20884412.6 dated Nov. 8, 2023, pp. 1-8.

* cited by examiner

SEQUENCE LISTING

<160> NUMBER OF SEQ ID NOS: 15

<210> SEQ ID NO 1
<211> LENGTH: 1812
<212> TYPE: DNA
<213> ORGANISM: Physiological type of Cinnamomum burmannii (Dryobalanops
      aromatica)

<400> SEQUENCE: 1

```
atggcgttgc aaatgactgt tccatttcta tcctccttcc tcccaaatcc tcgacacaga      60
cccacagccc atggtttcat accccaggaa cgtgtctcaa agcatatttc atgctccact     120
actacaccaa cctactcaac cacagtaccc agaagatcag gaaactacaa gcccagtata     180
tgggactatg attttgtgca gtcactagta agtgactaca aggtagaggc acatggaact     240
cgtgtggaga agttgaagga agttgtaaag aatttgttga aagaaacaga tagttctttg     300
gcccaaatgg aactgattga cagtctccat cgtctaggtg tgaggtggct ctttgaaaat     360
gagattaagc aagtgctata cactgtatca tcagacaaca ccagcataga aatgaagaaa     420
gatcttcatg cagtatcaac tcgatttaga cttcttagac aacatggggtt caaggtctcc     480
```

-continued

```
acagatgttt tcaatgactt cgaagatgaa aagggttgtt tcaagccaag cctttcaatg      540
gacataaagg gaatgctgag cttgtatgaa gcttcacacc ttgcctttca aggggagact      600
atattggatg aggcaagagc tttcacacac gcacatctca tgggtatcaa ggagaacata      660
gacccaatca ttcataaaaa agtagagcat gctttggata tgcctttgca ttggaggtta      720
gaaaaattag aggctaggtg gtacatggac atgtatatga gggaagaagg catgaattct      780
tctttgcttg aattggccat gcttcatttc aacattgtgc aagcaacatt ccaaacaaat      840
ttaaagagtt tgtcaaggtg gtggaaagat ttgggtcttg agagcagtt gagctttct       900 agagacaggt tggtggaatg tttcttttgg gcagccgcaa tgcatccga gccacaattt       960 ggacgttgcc aggaagctgt agcgaaagtt gttcaactca caacaacaat tgacgatatc     1020
tatgacgtgt atggtacggt ggatgagctg gaactttta ctaatgcggt tgatagatgg      1080
gatcttgagg caatggagca acttcctgaa tatatgaaga cctgtttctt agctttatac     1140
aacagtatta atgaaatagg ttatggaatt ttgaaagagc aagggcgtaa tgtcatacca     1200
taccttagaa atgcgtggac agaattgtgt aaagcatact tagtggaggc caaatggtat     1260
agtagtggat atacaccaat gcttgaggag tttctgcaaa cctcatggat ttcggttgga     1320
agtctaccca tgcaaacgta tgcttttgct ttacttgggc aaaatctagc accggagagc     1380
tgtgatttcg ctgagcagat ctcagatatc ttaccattgg caggaatgct aattcgattt     1440
ccagatgatt tgggaacttc attggatgaa ctaaagagag gtgatgttcc aaaatccatt     1500
cagtgttaca tgcatgaagc aggtgttaca gaggatgttg ctcgtgacca cataatgggt     1560
ctatttagag agacatggaa gaaactcaat gaataccttg tggaaagttc tattccccat     1620
gccttcatcg atcaagctat gaatcttggg cgtgtctcct attgtactta caaacatgga     1680
gatggattta gtgatggatt tggagatcct ggcagtcaag agaaaaagat gtacatgtct     1740
ttatttgttg aacccattca agttgatgaa gccaagggta tttcattttg tgtcgatggt     1800
ggatatgcct ga                                                        1812
```

```
<210> SEQ ID NO 2
<211> LENGTH: 603
<212> TYPE: PRT
<213> ORGANISM: Physiological type of Cinnamomum burmannii (Dryobalanops
      aromatica)

<400> SEQUENCE: 2

Met Ala Leu Gln Met Thr Val Pro Phe Leu Ser Ser Phe Leu Pro Asn
1               5                   10                  15

Pro Arg His Arg Pro Thr Ala His Gly Phe Ile Pro Gln Glu Arg Val
            20                  25                  30

Ser Lys His Ile Ser Cys Ser Thr Thr Thr Pro Thr Tyr Ser Thr Thr
        35                  40                  45

Val Pro Arg Arg Ser Gly Asn Tyr Lys Pro Ser Ile Trp Asp Tyr Asp
    50                  55                  60

Phe Val Gln Ser Leu Val Ser Asp Tyr Lys Val Glu Ala His Gly Thr
65                  70                  75                  80

Arg Val Glu Lys Leu Lys Glu Val Val Lys Asn Leu Leu Lys Glu Thr
                85                  90                  95

Asp Ser Ser Leu Ala Gln Met Glu Leu Ile Asp Ser Leu His Arg Leu
            100                 105                 110

Gly Val Arg Trp Leu Phe Glu Asn Glu Ile Lys Gln Val Leu Tyr Thr
        115                 120                 125
```

```
Val Ser Ser Asp Asn Thr Ser Ile Glu Met Lys Lys Asp Leu His Ala
    130                 135                 140

Val Ser Thr Arg Phe Arg Leu Leu Arg Gln His Gly Phe Lys Val Ser
145                 150                 155                 160

Thr Asp Val Phe Asn Asp Phe Glu Asp Glu Lys Gly Cys Phe Lys Pro
                165                 170                 175

Ser Leu Ser Met Asp Ile Lys Gly Met Leu Ser Leu Tyr Glu Ala Ser
                180                 185                 190

His Leu Ala Phe Gln Gly Glu Thr Ile Leu Asp Glu Ala Arg Ala Phe
                195                 200                 205

Thr His Ala His Leu Met Gly Ile Lys Glu Asn Ile Asp Pro Ile Ile
    210                 215                 220

His Lys Lys Val Glu His Ala Leu Asp Met Pro Leu His Trp Arg Leu
225                 230                 235                 240

Glu Lys Leu Glu Ala Arg Trp Tyr Met Asp Met Tyr Met Arg Glu Glu
                245                 250                 255

Gly Met Asn Ser Ser Leu Leu Glu Leu Ala Met Leu His Phe Asn Ile
                260                 265                 270

Val Gln Ala Thr Phe Gln Thr Asn Leu Lys Ser Leu Ser Arg Trp Trp
                275                 280                 285

Lys Asp Leu Gly Leu Gly Glu Gln Leu Ser Phe Ser Arg Asp Arg Leu
    290                 295                 300

Val Glu Cys Phe Phe Trp Ala Ala Ala Met Thr Ser Glu Pro Gln Phe
305                 310                 315                 320

Gly Arg Cys Gln Glu Ala Val Ala Lys Val Val Gln Leu Thr Thr Thr
                325                 330                 335

Ile Asp Asp Ile Tyr Asp Val Tyr Gly Thr Val Asp Glu Leu Glu Leu
                340                 345                 350

Phe Thr Asn Ala Val Asp Arg Trp Asp Leu Glu Ala Met Glu Gln Leu
                355                 360                 365

Pro Glu Tyr Met Lys Thr Cys Phe Leu Ala Leu Tyr Asn Ser Ile Asn
    370                 375                 380

Glu Ile Gly Tyr Gly Ile Leu Lys Glu Gln Gly Arg Asn Val Ile Pro
385                 390                 395                 400

Tyr Leu Arg Asn Ala Trp Thr Glu Leu Cys Lys Ala Tyr Leu Val Glu
                405                 410                 415

Ala Lys Trp Tyr Ser Ser Gly Tyr Thr Pro Met Leu Glu Glu Phe Leu
                420                 425                 430

Gln Thr Ser Trp Ile Ser Val Gly Ser Leu Pro Met Gln Thr Tyr Ala
                435                 440                 445

Phe Ala Leu Leu Gly Gln Asn Leu Ala Pro Glu Ser Cys Asp Phe Ala
    450                 455                 460

Glu Gln Ile Ser Asp Ile Leu Pro Leu Ala Gly Met Leu Ile Arg Phe
465                 470                 475                 480

Pro Asp Asp Leu Gly Thr Ser Leu Asp Glu Leu Lys Arg Gly Asp Val
                485                 490                 495

Pro Lys Ser Ile Gln Cys Tyr Met His Glu Ala Gly Val Thr Glu Asp
                500                 505                 510

Val Ala Arg Asp His Ile Met Gly Leu Phe Arg Glu Thr Trp Lys Lys
                515                 520                 525

Leu Asn Glu Tyr Leu Val Glu Ser Ser Ile Pro His Ala Phe Ile Asp
    530                 535                 540

Gln Ala Met Asn Leu Gly Arg Val Ser Tyr Cys Thr Tyr Lys His Gly
```

-continued

---

```
545              550              555              560

Asp Gly Phe Ser Asp Gly Phe Gly Asp Pro Gly Ser Gln Glu Lys Lys
                565              570              575

Met Tyr Met Ser Leu Phe Val Glu Pro Ile Gln Val Asp Glu Ala Lys
                580              585              590

Gly Ile Ser Phe Cys Val Asp Gly Gly Tyr Ala
                595              600

<210> SEQ ID NO 3
<211> LENGTH: 767
<212> TYPE: PRT
<213> ORGANISM: Artificial Sequence
<220> FEATURE:
<223> OTHER INFORMATION: Fusion protein

<400> SEQUENCE: 3

Met Ser Asp Lys Ile Ile His Leu Thr Asp Asp Ser Phe Asp Thr Asp
1               5               10              15

Val Leu Lys Ala Asp Gly Ala Ile Leu Val Asp Phe Trp Ala Glu Trp
                20              25              30

Cys Gly Pro Cys Lys Met Ile Ala Pro Ile Leu Asp Glu Ile Ala Asp
                35              40              45

Glu Tyr Gln Gly Lys Leu Thr Val Ala Lys Leu Asn Ile Asp Gln Asn
                50              55              60

Pro Gly Thr Ala Pro Lys Tyr Gly Ile Arg Gly Ile Pro Thr Leu Leu
65              70              75              80

Leu Phe Lys Asn Gly Glu Val Ala Ala Thr Lys Val Gly Ala Leu Ser
                85              90              95

Lys Gly Gln Leu Lys Glu Phe Leu Asp Ala Asn Leu Ala Gly Ser Gly
                100             105             110

Ser Gly His Met His His His His His His Ser Ser Gly Leu Val Pro
                115             120             125

Arg Gly Ser Gly Met Lys Glu Thr Ala Ala Ala Lys Phe Glu Arg Gln
                130             135             140

His Met Asp Ser Pro Asp Leu Gly Thr Asp Asp Asp Asp Lys Ala Met
145             150             155             160

Ala Asp Ile Gly Met Ala Leu Gln Met Thr Val Pro Phe Leu Ser Ser
                165             170             175

Phe Leu Pro Asn Pro Arg His Arg Pro Thr Ala His Gly Phe Ile Pro
                180             185             190

Gln Glu Arg Val Ser Lys His Ile Ser Cys Ser Thr Thr Thr Pro Thr
                195             200             205

Tyr Ser Thr Thr Val Pro Arg Arg Ser Gly Asn Tyr Lys Pro Ser Ile
                210             215             220

Trp Asp Tyr Asp Phe Val Gln Ser Leu Val Ser Asp Tyr Lys Val Glu
225             230             235             240

Ala His Gly Thr Arg Val Glu Lys Leu Lys Glu Val Val Lys Asn Leu
                245             250             255

Leu Lys Glu Thr Asp Ser Ser Leu Ala Gln Met Glu Leu Ile Asp Ser
                260             265             270

Leu His Arg Leu Gly Val Arg Trp Leu Phe Glu Asn Glu Ile Lys Gln
                275             280             285

Val Leu Tyr Thr Val Ser Ser Asp Asn Thr Ser Ile Glu Met Lys Lys
                290             295             300

Asp Leu His Ala Val Ser Thr Arg Phe Arg Leu Leu Arg Gln His Gly
```

-continued

```
305                     310                     315                     320
Phe Lys Val Ser Thr Asp Val Phe Asn Asp Phe Glu Asp Glu Lys Gly
                325                     330                     335

Cys Phe Lys Pro Ser Leu Ser Met Asp Ile Lys Gly Met Leu Ser Leu
                340                     345                     350

Tyr Glu Ala Ser His Leu Ala Phe Gln Gly Glu Thr Ile Leu Asp Glu
                355                     360                     365

Ala Arg Ala Phe Thr His Ala His Leu Met Gly Ile Lys Glu Asn Ile
                370                     375                     380

Asp Pro Ile Ile His Lys Lys Val Glu His Ala Leu Asp Met Pro Leu
385                     390                     395                     400

His Trp Arg Leu Glu Lys Leu Glu Ala Arg Trp Tyr Met Asp Met Tyr
                405                     410                     415

Met Arg Glu Glu Gly Met Asn Ser Ser Leu Leu Glu Leu Ala Met Leu
                420                     425                     430

His Phe Asn Ile Val Gln Ala Thr Phe Gln Thr Asn Leu Lys Ser Leu
                435                     440                     445

Ser Arg Trp Trp Lys Asp Leu Gly Leu Gly Glu Gln Leu Ser Phe Ser
                450                     455                     460

Arg Asp Arg Leu Val Glu Cys Phe Phe Trp Ala Ala Ala Met Thr Ser
465                     470                     475                     480

Glu Pro Gln Phe Gly Arg Cys Gln Glu Ala Val Ala Lys Val Val Gln
                485                     490                     495

Leu Thr Thr Thr Ile Asp Asp Ile Tyr Asp Val Tyr Gly Thr Val Asp
                500                     505                     510

Glu Leu Glu Leu Phe Thr Asn Ala Val Asp Arg Trp Asp Leu Glu Ala
                515                     520                     525

Met Glu Gln Leu Pro Glu Tyr Met Lys Thr Cys Phe Leu Ala Leu Tyr
                530                     535                     540

Asn Ser Ile Asn Glu Ile Gly Tyr Gly Ile Leu Lys Glu Gln Gly Arg
545                     550                     555                     560

Asn Val Ile Pro Tyr Leu Arg Asn Ala Trp Thr Glu Leu Cys Lys Ala
                565                     570                     575

Tyr Leu Val Glu Ala Lys Trp Tyr Ser Ser Gly Tyr Thr Pro Met Leu
                580                     585                     590

Glu Glu Phe Leu Gln Thr Ser Trp Ile Ser Val Gly Ser Leu Pro Met
                595                     600                     605

Gln Thr Tyr Ala Phe Ala Leu Leu Gly Gln Asn Leu Ala Pro Glu Ser
                610                     615                     620

Cys Asp Phe Ala Glu Gln Ile Ser Asp Ile Leu Pro Leu Ala Gly Met
625                     630                     635                     640

Leu Ile Arg Phe Pro Asp Asp Leu Gly Thr Ser Leu Asp Glu Leu Lys
                645                     650                     655

Arg Gly Asp Val Pro Lys Ser Ile Gln Cys Tyr Met His Glu Ala Gly
                660                     665                     670

Val Thr Glu Asp Val Ala Arg Asp His Ile Met Gly Leu Phe Arg Glu
                675                     680                     685

Thr Trp Lys Lys Leu Asn Glu Tyr Leu Val Glu Ser Ser Ile Pro His
                690                     695                     700

Ala Phe Ile Asp Gln Ala Met Asn Leu Gly Arg Val Ser Tyr Cys Thr
705                     710                     715                     720

Tyr Lys His Gly Asp Gly Phe Ser Asp Gly Phe Gly Asp Pro Gly Ser
                725                     730                     735
```

```
Gln Glu Lys Lys Met Tyr Met Ser Leu Phe Val Glu Pro Ile Gln Val
        740                 745                 750

Asp Glu Ala Lys Gly Ile Ser Phe Cys Val Asp Gly Gly Tyr Ala
        755                 760                 765

<210> SEQ ID NO 4
<211> LENGTH: 2304
<212> TYPE: DNA
<213> ORGANISM: Artificial Sequence
<220> FEATURE:
<223> OTHER INFORMATION: Fusion gene encoding the fusion protein

<400> SEQUENCE: 4
atgagcgata aaattattca cctgactgac gacagttttg acacggatgt actcaaagcg       60
gacggggcga tcctcgtcga tttctgggca gagtggtgcg gtccgtgcaa aatgatcgcc      120
ccgattctgg atgaaatcgc tgacgaatat cagggcaaac tgaccgttgc aaaactgaac      180
atcgatcaaa accctggcac tgcgccgaaa tatggcatcc gtggtatccc gactctgctg      240
ctgttcaaaa acggtgaagt ggcggcaacc aaagtgggtg cactgtctaa aggtcagttg      300
aaagagttcc tcgacgctaa cctggccggt tctggttctg gccatatgca ccatcatcat      360
catcattctt ctggtctggt gccacgcggt tctggtatga agaaaccgc tgctgctaaa       420 ttcgaacgcc agcacatgga cagcccagat ctgggtaccg acgacgacga caaggccatg      480
gctgatatcg aatggcgtt gcaaatgact gttccatttc tatcctcctt cctcccaaat       540
cctcgacaca gacccacagc ccatggtttc tacccccagg aacgtgtctc aaagcatatt      600
tcatgctcca ctactacacc aacctactca accacagtac ccagaagatc aggaaactac      660
aagcccagta tatgggacta tgattttgtg cagtcactag taagtgacta caaggtagag      720
gcacatggaa ctcgtgtgga gaagttgaag gaagttgtaa agaatttgtt gaaagaaaca      780
gatagttctt tggcccaaat ggaactgatt gacagtctcc atcgtctagg tgtgaggtgg      840
ctctttgaaa atgagattaa gcaagtgcta tacactgtat catcagacaa caccagcata      900
gaaatgaaga aagatcttca tgcagtatca actcgattta gacttcttag acaacatggg      960
ttcaaggtct ccacagatgt tttcaatgac ttcgaagatg aaaaggggttg tttcaagcca     1020 agcctttcaa tggacataaa gggaatgctg agcttgtatg aagcttcaca ccttgccttt     1080
caaggggaga ctatattgga tgaggcaaga gctttcacac acgcacatct catgggtatc     1140
aaggagaaca tagacccaat cattcataaa aaagtagagc atgctttgga tatgcctttg     1200
cattggaggt tagaaaaatt agaggctagg tggtacatgg acatgtatat gagggaagaa     1260
ggcatgaatt cttctttgct tgaattggcc atgcttcatt tcaacattgt gcaagcaaca     1320
ttccaaacaa atttaaagag tttgtcaagg tggtggaaag atttgggtct ggagagcag      1380 ttgagctttt ctagagacag gttggtggaa tgtttctttt gggcagccgc aatgacatcc     1440
gagccacaat ttggacgttg ccaggaagct gtagcgaaag ttgttcaact cacaacaaca     1500
attgacgata tctatgacgt gtatggtacg gtggatgagc tggaactttt tactaatgcg     1560
gttgatagat gggatcttga ggcaatggag caacttcctg aatatatgaa gacctgtttc     1620
ttagctttat acaacagtat taatgaaata ggttatggaa ttttgaaaga gcaagggcgt     1680
aatgtcatac cataccttag aaatgcgtgg acagaattgt gtaaagcata cttagtggag     1740
gccaaatggt atagtagtgg atatacacca atgcttgagg agtttctgca aacctcatgg     1800
atttcggttg gaagtctacc catgcaaacg tatgctttgt ctttacttgg gcaaaatcta     1860
```

-continued

```
gcaccggaga gctgtgattt cgctgagcag atctcagata tcttaccatt ggcaggaatg   1920
ctaattcgat ttccagatga tttgggaact tcattggatg aactaaagag aggtgatgtt   1980
ccaaaatcca ttcagtgtta catgcatgaa gcaggtgtta cagaggatgt tgctcgtgac   2040
cacataatgg gtctatttag agagacatgg aagaaactca atgaatacct tgtggaaagt   2100
tctattcccc atgccttcat cgatcaagct atgaatcttg ggcgtgtctc ctattgtact   2160
tacaaacatg gagatggatt tagtgatgga tttggagatc ctggcagtca agagaaaaag   2220
atgtacatgt ctttatttgt tgaacccatt caagttgatg aagccaaggg tatttcattt   2280
tgtgtcgatg gtggatatgc ctga                                         2304

<210> SEQ ID NO 5
<211> LENGTH: 1721
<212> TYPE: DNA
<213> ORGANISM: Artificial Sequence
<220> FEATURE:
<223> OTHER INFORMATION: Ura3 marker

<400> SEQUENCE: 5
ataaagcagc cgctaccaaa cagacaagat tcagtatgta aggtaaatac cttttttgcac    60 agttaaacta cccaaactta ttaaagcttg ataaattact gaaattccac ctttcagtta   120
gattcaggcc tcatatagat tagatatagg gtacgtaaca ttctgtcaac caagttgttg   180
gaatgaaagt ctaaaatgtc atctattcgg tagcactcat gttactagta tactgtcaca   240
tgcggtgtaa cgtggggaca taaaacagac atcaaatata atggaagctg aaatgcaaag   300
atcgataatg taataggaat gaaacatata aaacgaaagg agaagtaatg gtaatattag   360
tatgtagaaa taccgattca attttgggga ttcttatatt ctcgagagaa tttctagtat   420
aatctgtata cataatatta taggctttac caaaccacag cttttcaatt caattcatca   480
tttttttttt attctttttt ttgatttcgg tttctttgaa attttttttga ttcggtaatc   540 tccgaacaga aggaagaacg aaggaaggag cacagactta gattggtata tatacgcata   600
tgtagtgttg aagaaacatg aaattgccca gtattcttaa cccaactgca cagaacaaaa   660
acctgcagga aacgaagata aatcatgtcg aaagctacat ataaggaacg tgctgctact   720
catcctagtc ctgttgctgc caagctattt aatatcatgc acgaaaagca aacaaacttg   780
tgtgcttcat tggatgttcg taccaccaag gaattactgg agttagttga agcattaggt   840
cccaaaattt gtttactaaa aacacatgtg gatatcttga ctgatttttc catggagggc   900
acagttaagc cgctaaaggc attatccgcc aagtacaatt ttttactctt cgaagacaga   960
aaatttgctg acattggtaa tacagtcaaa ttgcagtact ctgcgggtgt atacagaata  1020
gcagaatggg cagacattac gaatgcacac ggtgtggtgg cccaggtat tgttagcggt   1080 ttgaagcagg cggcagaaga agtaacaaag gaacctagag gccttttgat gttagcagaa  1140
ttgtcatgca agggctccct atctactgga gaatatacta agggtactgt tgacattgcg  1200
aagagcgaca aagattttgt tatcggcttt attgctcaaa gagacatggg tggaagagat  1260
gaaggttacg attggttgat tatgacaccc ggtgtgggtt tagatgacaa gggagacgca  1320
ttgggtcaac agtatagaac cgtggatgat gtggtctcta caggatctga cattattatt  1380
gttggaagag gactatttgc aaagggaagg gatgctaagg tagagggtga acgttacaga  1440
aaagcaggct gggaagcata tttgagaaga tgcggccagc aaaactaaaa aactgtatta  1500
taagtaaatg catgtatact aaactcacaa attagagctt caatttaatt atatcagtta  1560 ttacccctatg cccccggtcc gtttgttcta tacttctctc tgctatacct acaagcaagg  1620
```

-continued

```
taatcggaag tagtattacg caggaatatc ccgcgcgaag ctacaatttt tggactccaa    1680
cgtcaaagca ggggagtcag aagtcccctc taaaattgcc t                       1721

<210> SEQ ID NO 6
<211> LENGTH: 2785
<212> TYPE: DNA
<213> ORGANISM: Artificial Sequence
<220> FEATURE:
<223> OTHER INFORMATION: PTDH3-tHMGR1-TTPI1

<400> SEQUENCE: 6
atactagcgt tgaatgttag cgtcaacaac aagaagttta atgacgcgga ggccaaggca      60
aaaagattcc ttgattacgt aagggagtta gaatcatttt gaataaaaaa cacgcttttt     120
cagttcgagt ttatcattat caatactgcc atttcaaaga atacgtaaat aattaatagt     180
agtgattttc ctaactttat ttagtcaaaa aattagcctt ttaattctgc tgtaacccgt     240
acatgcccaa aatagggggc gggttacaca gaatatataa catcgtaggt gtctgggtga     300
acagtttatt cctggcatcc actaaatata atggagcccg cttttttaagc tggcatccag     360 aaaaaaaaag aatcccagca ccaaaatatt gttttcttca ccaaccatca gttcataggt     420
ccattctctt agcgcaacta cagagaacag gggcacaaac aggcaaaaaa cgggcacaac     480
ctcaatggag tgatgcaacc tgcctggagt aaatgatgac acaaggcaat tgacccacgc     540
atgtatctat ctcattttct tacaccttct attaccttct gctctctctg atttggaaaa     600
agctgaaaaa aaaggttgaa accagttccc tgaaattatt cccctacttg actaataagt     660
atataaagac ggtaggtatt gattgtaatt ctgtaaatct atttcttaaa cttcttaaat     720 tctacttta tagttagtct tttttttagt tttaaaacac caagaactta gtttcgaata     780
aacacacata aacaaacaaa atggctgcag accaattggt gaaaactgaa gtcaccaaga     840
agtcttttac tgctcctgta caaaaggctt ctacaccagt tttaaccaat aaaacagtca     900
tttctggatc gaaagtcaaa agtttatcat ctgcgcaatc gagctcatca ggaccttcat     960
catctagtga ggaagatgat tcccgcgata ttgaaagctt ggataagaaa atacgtcctt    1020
tagaagaatt agaagcatta ttaagtagtg gaaatacaaa acaattgaag aacaaagagg    1080
tcgctgcctt ggttattcac ggtaagttac ctttgtacgc tttggagaaa aaattaggtg    1140
atactacgag agcggttgcg gtacgtagga aggctctttc aattttggca gaagctcctg    1200
tattagcatc tgatcgttta ccatataaaa attatgacta cgaccgcgta tttggcgctt    1260
gttgtgaaaa tgttataggt tacatgcctt tgcccgttgg tgttataggc cccttggtta    1320
tcgatggtac atcttatcat ataccaatgg caactacaga gggttgtttg gtagcttctg    1380
ccatgcgtgg ctgtaaggca atcaatgctg cggtggtgc aacaactgtt ttaactaagg    1440
atggtatgac aagaggccca gtagtccgtt tcccaacttt gaaaagatct ggtgcctgta    1500
agatatggtt agactcagaa gagggacaaa acgcaattaa aaaagctttt aactctacat    1560
caagatttgc acgtctgcaa catattcaaa cttgtctagc aggagattta ctcttcatga    1620
gatttagaac aactactggt gacgcaatgg gtatgaatat gatttctaaa ggtgtcgaat    1680
actcattaaa gcaaatggta gaagagtatg ctgggaaga tatggaggtt gtctccgttt    1740
ctggtaacta ctgtaccgac aaaaaaccag ctgccatcaa ctggatcgaa ggtcgtggta    1800
agagtgtcgt cgcagaagct actattcctg gtgatgttgt cagaaaagtg ttaaaaagtg    1860
atgtttccgc attggttgag ttgaacattg ctaagaattt ggttggatct gcaatggctg    1920
```

-continued

```
ggtctgttgg tggatttaac gcacatgcag ctaatttagt gacagctgtt ttcttggcat     1980
taggacaaga tcctgcacaa aatgttgaaa gttccaactg tataacattg atgaaagaag     2040
tggacggtga tttgagaatt tccgtatcca tgccatccat cgaagtaggt accatcggtg     2100
gtggtactgt tctagaacca caaggtgcca tgttggactt attaggtgta agaggcccgc     2160
atgctaccgc tcctggtacc aacgcacgtc aattagcaag aatagttgcc tgtgccgtct     2220
tggcaggtga attatcctta tgtgctgccc tagcagccgg ccatttggtt caaagtcata     2280
tgacccacaa caggaaacct gctgaaccaa caaaacctaa caatttggac gccactgata     2340
taaatcgttt gaaagatggg tccgtcacct gcattaaatc ctaagattaa tataattata     2400
taaaaatatt atcttctttt ctttatatct agtgttatgt aaaataaatt gatgactacg     2460
gaaagctttt ttatattgtt tcttttttcat tctgagccac ttaaatttcg tgaatgttct     2520
tgtaagggac ggtagattta caagtgatac aacaaaaagc aaggcgcttt ttctaataaa     2580
aagaagaaaa gcatttaaca attgaacacc tctatatcaa cgaagaatat tactttgtct     2640
ctaaatcctt gtaaaatgtg tacgatctct atatgggtta ctcataagtg taccgaagac     2700
tgcattgaaa gtttatgttt tttcactgga ggcgtcattt tcgcgttgag aagatgttct     2760
tatccaaatt tcaactgtta tatag                                          2785
```

```
<210> SEQ ID NO 7
<211> LENGTH: 1886
<212> TYPE: DNA
<213> ORGANISM: Artificial Sequence
<220> FEATURE:
<223> OTHER INFORMATION: PADH1-IDI1-TPGI

<400> SEQUENCE: 7
```

```
acatgtaggt ggcggagggg agatatacaa tagaacagat accagacaag acataatggg       60
ctaaacaaga ctacaccaat tacactgcct cattgatggt ggtacataac gaactaatac      120
tgtagcccta gacttgatag ccatcatcat atcgaagttt cactacccct tttccatttg      180
ccatctattg aagtaataat aggcgcatgc aacttctttt cttttttttt cttttctctc      240
tcccccgttg ttgtctcacc atatccgcaa tgacaaaaaa atgatggaag acactaaagg      300
aaaaaattaa cgacaaagac agcaccaaca gatgtcgttg ttccagagct gatgaggggt      360
atctcgaagc acacgaaact tttttccttcc ttcattcacg cacactactc tctaatgagc     420
aacggtatac ggccttcctt ccagttactt gaatttgaaa taaaaaaag tttgctgtct       480 tgctatcaag tataaataga cctgcaatta ttaatctttt gtttcctcgt cattgttctc     540
gttccctttc ttccttgttt ctttttctgc acaatatttc aagctatacc aagcatacaa     600
tcaactatct catatacaat gactgccgac aacaatagta tgccccatgg tgcagtatct      660
agttacgcca aattagtgca aaaccaaaca cctgaagaca ttttggaaga gtttcctgaa      720
attattccat tacaacaaag acctaatacc cgatctagtg agacgtcaaa tgacgaaagc      780
ggagaaacat gttttctgg tcatgatgag gagcaaatta agttaatgaa tgaaaattgt       840 attgtttgg attgggacga taatgctatt ggtgccggta ccaagaaagt ttgtcattta       900
atggaaaata ttgaaaaggg tttactacat cgtgcattct ccgtctttat tttcaatgaa     960
caaggtgaat tacttttaca acaaagagcc actgaaaaaa taactttccc tgatctttgg     1020
actaacacat gctgctctca tccactatgt attgatgacg aattaggttt gaagggtaag     1080
ctagacgata agattaaggg cgctattact gcggcggtga aaaactaga tcatgaatta      1140 ggtattccag aagatgaaac taagacaagg ggtaagtttc acttttttaaa cagaatccat    1200
```

```
tacatggcac caagcaatga accatggggt gaacatgaaa ttgattacat cctattttat      1260
aagatcaacg ctaaagaaaa cttgactgtc aacccaaacg tcaatgaagt tagagacttc      1320
aaatgggttt caccaaatga tttgaaaact atgtttgctg acccaagtta caagtttacg      1380
ccttggttta agattatttg cgagaattac ttattcaact ggtgggagca attagatgac      1440
ctttctgaag tggaaaatga caggcaaatt catagaatgc tataaaacaa atcgctctta      1500
aatatatacc taaagaacat taaagctata ttataagcaa agatacgtaa attttgctta      1560
tattattata cacatatcat atttctatat ttttaagatt tggttatata atgtacgtaa      1620
tgcaaaggaa ataaatttta tacattattg aacagcgtcc aagtaactac attatgtgca      1680
ctaatagttt agcgtcgtga agactttatt gtgtcgcgaa aagtaaaaat tttaaaaatt      1740
agagcacctt gaacttgcga aaaaggttct catcaactgt ttaaaaggag gatatcaggt      1800
cctatttctg acaaacaata tacaaattta gtttcaaaga tgaatcagtg cgcgaaggac      1860
ataactcatg aagcctccag tatacc                                           1886
```

<210> SEQ ID NO 8
<211> LENGTH: 2492
<212> TYPE: DNA
<213> ORGANISM: Artificial Sequence
<220> FEATURE:
<223> OTHER INFORMATION: PPGK1-tHMGR1-TADH1

<400> SEQUENCE: 8

```
acgcacagat attataacat ctgcacaata ggcatttgca agaattactc gtgagtaagg       60
aaagagtgag gaactatcgc atacctgcat ttaaagatgc cgatttgggc gcgaatcctt      120
tattttggct tcaccctcat actattatca gggccagaaa aaggaagtgt ttccctcctt      180
cttgaattga tgttaccctc ataaagcacg tggcctctta tcgagaaaga aattaccgtc      240
gctcgtgatt tgtttgcaaa aagaacaaaa ctgaaaaaac ccagacacgc tcgacttcct      300
gtcttcctat tgattgcagc ttccaatttc gtcacacaac aaggtcctag cgacggctca      360
caggttttgt aacaagcaat cgaaggttct ggaatggcgg gaaagggttt agtaccacat      420
gctatgatgc ccactgtgat ctccagagca aagttcgttc gatcgtactg ttactctctc      480
tctttcaaac agaattgtcc gaatcgtgtg acaacaacag cctgttctca cacactcttt      540
tcttctaacc aaggggtgg tttagtttag tagaacctcg tgaaacttac atttacatat      600
atataaactt gcataaattg gtcaatgcaa gaaatacata tttggtcttt ctaattcgt       660 agtttttcaa gttcttagat gctttctttt tctctttttt acagatcatc aaggaagtaa      720
ttatctactt tttacaacaa atataaaaca atggctgcag accaattggt gaaaactgaa      780
gtcaccaaga agtcttttac tgctcctgta caaaaggctt ctacaccagt tttaaccaat      840
aaaacagtca tttctggatc gaaagtcaaa agtttatcat ctgcgcaatc gagctcatca      900
ggaccttcat catctagtga ggaagatgat tcccgcgata ttgaaagctt ggataagaaa      960
atacgtcctt tagaagaatt agaagcatta ttaagtagtg aaatacaaa acaattgaag     1020 aacaaagagg tcgctgcctt ggttattcac ggtaagttac ctttgtacgc tttggagaaa     1080
aaattaggtg atactacgag agcggttgcg gtacgtagga aggctctttc aattttggca     1140
gaagctcctg tattagcatc tgatcgttta ccatataaaa attatgacta cgaccgcgta     1200
tttggcgctt gttgtgaaaa tgttataggt tacatgcctt gcccgttggg tgttataggc     1260
cccttggtta tcgatggtac atcttatcat ataccaatgg caactacaga gggttgtttg     1320
```

-continued

```
gtagcttctg ccatgcgtgg ctgtaaggca atcaatgctg gcggtggtgc aacaactgtt      1380
ttaactaagg atggtatgac aagaggccca gtagtccgtt tcccaacttt gaaaagatct      1440
ggtgcctgta agatatggtt agactcagaa gagggacaaa acgcaattaa aaaagctttt      1500
aactctacat caagatttgc acgtctgcaa catattcaaa cttgtctagc aggagattta      1560
ctcttcatga gatttagaac aactactggt gacgcaatgg gtatgaatat gatttctaaa      1620
ggtgtcgaat actcattaaa gcaaatggta gaagagtatg gctgggaaga tatggaggtt      1680
gtctccgttt ctggtaacta ctgtaccgac aaaaaaccag ctgccatcaa ctggatcgaa      1740
ggtcgtggta agagtgtcgt cgcagaagct actattcctg gtgatgttgt cagaaaagtg      1800
ttaaaaagtg atgtttccgc attggttgag ttgaacattg ctaagaattt ggttggatct      1860
gcaatggctg ggtctgttgg tggatttaac gcacatgcag ctaatttagt gacagctgtt      1920
ttcttggcat taggacaaga tcctgcacaa aatgttgaaa gttccaactg tataacattg      1980
atgaaagaag tggacggtga tttgagaatt tccgtatcca tgccatccat cgaagtaggt      2040
accatcggtg gtggtactgt tctagaacca caaggtgcca tgttggactt attaggtgta      2100
agaggcccgc atgctaccgc tcctggtacc aacgcacgtc aattagcaag aatagttgcc      2160
tgtgccgtct tggcaggtga attatcctta tgtgctgccc tagcagccgg ccatttggtt      2220
caaagtcata tgacccacaa caggaaacct gctgaaccaa caaaacctaa caatttggac      2280
gccactgata taaatcgttt gaaagatggg tccgtcacct gcattaaatc ctaaagttat      2340
aaaaaaaata agtgtataca aatttttaaag tgactcttag gttttaaaac gaaaattctt      2400
attcttgagt aactctttcc tgtaggtcag gttgctttct caggtatagc atgaggtcgc      2460
tcttattgac cacacctcta ccggcatgcc ga                                    2492
```

<210> SEQ ID NO 9
<211> LENGTH: 2445
<212> TYPE: DNA
<213> ORGANISM: Artificial Sequence
<220> FEATURE:
<223> OTHER INFORMATION: PTEF2-ERG20F96W-N127W-TCYC1

<400> SEQUENCE: 9

```
tatacttaca tatagtagat gtcaagcgta ggcgcttccc ctgccggctg tgagggcgcc       60
ataaccaagg tatctataga ccgccaatca gcaaactacc tccgtacatt catgttgcac      120
ccacacattt atacacccag accgcgacaa attacccata aggttgtttg tgacggcgtc      180
gtacaagaga acgtgggaac ttttttaggct caccaaaaaa gaaagaaaaa atacgagttg      240
ctgacagaag cctcaagaaa aaaaaaattc ttcttcgact atgctggagg cagagatgat      300
cgagccggta gttaactata tatagctaaa ttggttccat caccttcttt tctggtgtcg      360
ctccttctag tgctatttct ggcttttcct attttttttt ttccattttt ctttctctct      420
ttctaatata taaattctct tgcattttct attttttctct ctatctattc tacttgttta      480
ttcccttcaa ggttttttttt taaggagtac ttgttttttag aatatacggt caacgaacta      540
taattaacta aacactagta ccatggcttc agaaaaagaa attaggagag agagattctt      600
gaacgttttc cctaaattag tagaggaatt gaacgcatcg cttttggctt acggtatgcc      660
taaggaagca tgtgactggt atgcccactc attgaactac aacactccag gcggtaagct      720
aaatagaggt ttgtccgttg tggacacgta tgctattctc tccaacaaga ccgttgaaca      780
attggggcaa gaagaatacg aaaaggttgc cattctaggt tggtgcattg agttgttgca      840
ggcttactgg ttggtcgccg atgatatgat ggacaagtcc attaccagaa gaggccaacc      900
```

-continued

```
atgttggtac aaggttcctg aagttgggga aattgccatc tgggacgcat tcatgttaga      960
ggctgctatc tacaagcttt tgaaatctca cttcagaaac gaaaaatact acatagatat     1020
caccgaattg ttccatgagg tcaccttcca aaccgaattg ggccaattga tggacttaat     1080
cactgcacct gaagacaaag tcgacttgag taagttctcc ctaaagaagc actccttcat     1140
agttactttc aagactgctt actattcttt ctacttgcct gtcgcattgg ccatgtacgt     1200
tgccggtatc acggatgaaa aggatttgaa acaagccaga gatgtcttga ttccattggg     1260
tgaatacttc caaattcaag atgactactt agactgcttc ggtaccccag aacagatcgg     1320
taagatcggt acagatatcc aagataacaa atgttcttgg gtaatcaaca aggcattgga     1380
acttgcttcc gcagaacaaa gaaagacttt agacgaaaat tacggtaaga aggactcagt     1440
cgcagaagcc aaatgcaaaa agattttcaa tgacttgaaa attgaacagc tataccacga     1500
atatgaagag tctattgcca aggatttgaa ggccaaaatt tctcaggtcg atgagtctcg     1560
tggcttcaaa gctgatgtct taactgcgtt cttgaacaaa gtttacaaga gaagcaaata     1620
gtcatgtaat tagttatgtc acgcttacat tcacgccctc cccccacatc cgctctaacc     1680
gaaaaggaag gagttagaca acctgaagtc taggtccta tttattttt tatagttatg       1740 ttagtattaa gaacgttatt tatatttcaa attttctttt tttttctgta cagacgcgtg     1800
tacgcatgta acattatact gaaaaccttg cttgagaagg ttttgggacg ctcgaaggct     1860
ttaatttgca acgacggtag acgccaacta cgctgacaga ccgatttgtt taagattaga     1920
agatttttag ccgcgccgca atcggaacca gcaaactcaa ttctgggaac agtttaaaat     1980
actagtaatt acgatagccg agaaacggac taagtccgcc aatggaattt cgacaattat     2040
catattattc accaattaat cacaagttgg taatgagttt gataacaagt tactttctta     2100
acaacgttag tatcgtcaaa acactcggtt ttactcgagc ttgtagcaca ataataccgt     2160
gtagagttct gtattgttct tcttagtgct tgtatatgct catcccgacc ttccattttt     2220
tttttcttgg aatcagtaca tagcaggtat gagttgttag agctgttaca agttacggta     2280
aacatttcaa cacaccgtta tttaacgaat ttatttgaga aagtggtgta ttttaagata     2340
tatgtttggt ttcgattgtt ggcaaagact ataatattat gcatatagga tataccaaaa     2400
attctctctg aggatatagg aatctacaaa atgaatctac atttc                     2445
```

<210> SEQ ID NO 10  
<211> LENGTH: 24  
<212> TYPE: DNA  
<213> ORGANISM: Artificial sequence  
<220> FEATURE:  
<223> OTHER INFORMATION: Primer

<400> SEQUENCE: 10

```
atggcgttgc aaatgactgt tcca                                             24
```

<210> SEQ ID NO 11  
<211> LENGTH: 24  
<212> TYPE: DNA  
<213> ORGANISM: Artificial sequence  
<220> FEATURE:  
<223> OTHER INFORMATION: Primer

<400> SEQUENCE: 11

```
tcaggcatat ccaccatcga caca                                             24
```

<210> SEQ ID NO 12

-continued

```
<211> LENGTH: 41
<212> TYPE: DNA
<213> ORGANISM: Artificial sequence
<220> FEATURE:
<223> OTHER INFORMATION: Primer

<400> SEQUENCE: 12
ccatggctga tatcggaatg gcgttgcaaa tgactgttcc a                        41

<210> SEQ ID NO 13
<211> LENGTH: 41
<212> TYPE: DNA
<213> ORGANISM: Artificial sequence
<220> FEATURE:
<223> OTHER INFORMATION: Primer

<400> SEQUENCE: 13
acggagctcg aattcggtca ggcatatcca ccatcgacac a                        41

<210> SEQ ID NO 14
<211> LENGTH: 41
<212> TYPE: DNA
<213> ORGANISM: Artificial sequence
<220> FEATURE:
<223> OTHER INFORMATION: Primer

<400> SEQUENCE: 14
ccatggctga tatcggaatg gcgttgcaaa tgactgttcc a                        41

<210> SEQ ID NO 15
<211> LENGTH: 41
<212> TYPE: DNA
<213> ORGANISM: Artificial sequence
<220> FEATURE:
<223> OTHER INFORMATION: Primer

<400> SEQUENCE: 15
acggagctcg aattcggtca ggcatatcca ccatcgacac a                        41
```

CINNAMOMUM BURMANNII MONOTERPENE SYNTHASE CBTPS1, RELATED BIOMATERIAL THEREOF AND APPLICATION THEREOF

CROSS-REFERENCE TO RELATED APPLICATION

The present application is a U.S. national phase entry under 35 U.S.C. § 371 of International Application No. PCT/CN2020/126683 filed Nov. 5, 2020, which claims priority from Chinese Patent Application No. 201911082325.8 filed on Nov. 7, 2019, all of which are hereby incorporated by reference in its entirety.

TECHNICAL FIELD

The present invention belongs to the field of medicinal plant genetic engineering, and more particularly, relates to *Cinnamomum burmannii* monoterpene synthase CbTPS1 and related biological materials thereof and application thereof.

BACKGROUND OF THE INVENTION

Physiological type of *Cinnamomum burmannii* is an evergreen tree of the genus *Cinnamomum* in the family Lauraceae, rich in dextrorotatory borneol ((+)-borneol). It is a rare medicinal herb, and also a high-class spice, raw material for daily cosmetics, and chemical products. It is widely used in many industries such as medical, beauty, perfume and so on. The discovery of a new resource of natural dextrorotatory borneol with production and utilization value in Guangdong by the South China Botanical Garden of the Chinese Academy of Sciences has filled the gap in the production of natural dextrorotatory borneol in our country.

Natural borneol (dextrorotatory borneol, (+)-borneol) is an important Chinese medicine, with the effects of resuscitation and waking up the mind, relieving fever and pain. It is clinically used to treat burns, scalds, eye diseases, strokes and other diseases. It also has antibacterial, antioxidative, analgesic, anti-inflammatory, antipyretic, protection of cardiovascular, and cerebrovascular effects, etc. (Wang S, Zhang D, Hu J, et al. A clinical and mechanistic study of topical borneol-induced analgesia [J]. EMBO Molecular Medicine, 2017, 9 (6): 802-815; Tang S, Wang A, Yan X, et al. Brain-targeted intranasal delivery of dopamine with borneol and lactoferrin co-modified nanoparticles for treating Parkinson's disease [J]. Drug Deliv, 2019, 26(1): 700-707; Yu B, Zhong F M, Yao Y, et al. Synergistic protection of tetramethylpyrazine phosphate and borneol on brain microvascular endothelium cells injured by hypoxia [J]. Am J Transl Res. 2019, 11(4): 2168-2180.). It is also widely used in tobacco, daily use chemicals, food, pesticides and other fields (Shi S, Wu Q, Su J, et al. Composition analysis of volatile oils from flowers, leaves and branches of *Cinnamomum camphora* chvar. Borneol in China [J]. Journal of Essential Oil Research, 2013, 25(5): 7.). Due to the high price of natural borneol, many pharmaceutical companies use synthetic borneol instead of natural borneol, but synthetic borneol is chemically prepared from turpentine, and the product contains isoborneol. As people become more safety conscious, the demand for natural borneol (dextrorotatory borneol) is increasing. The slow growth of the physiological type of *Cinnamomum burmannii* plant, coupled with the low content of these active ingredients in the plant, has greatly limited its development.

Natural borneol (dextrorotatory borneol, (+)-borneol) is a bicyclic monoterpene compound, which belongs to the terpenoids. At the same time, the terpenoids are the main active ingredients of the physiological type of *Cinnamomum burmannii*, including dextrorotatory borneol ((+)-borneol), camphor and linalool. Through the cytosolic mevalonate (MVA) pathway and the plastidial 2-C-methyl-D-erythritol-4-phosphate (MEP) pathway, the universal substrates of terpenoids, i.e., isopentenyl pyrophosphate (IPP) and its isomer dimethylallyl pyrophosphate (DMAPP) are generated. From them, the substrates of monoterpenes, sesquiterpenes, diterpenes, triterpenes, i.e., geranyl diphosphate (GPP), farnesyl diphosphate (FPP) and geranylgeranyl diphosphate (GGPP) are generated. Monoterpene synthase, also known as monoterpene cyclase, can catalyze GPP to form various monoterpene backbones, and is considered to be a key enzyme in the synthesis of terpenoid secondary metabolism end products (Chen F, Tholl D, Bohlmann J, et al. The family of terpene synthases in plants: a mid-size family of genes for specialized metabolism that is highly diversified throughout the kingdom [J]. The Plant journal: for cell and molecular biology, 2011, 66(1): 212-229; Trapp S C, Croteau R. Genomic organization of plant terpene synthases and molecular evolutionary implications [J]. Genetics, 2001, 158: 811-832).

At present, there are reports on the transcriptome of the physiological type of *Cinnamomum burmannii*, and two candidate enzymes related to borneol biosynthesis have been screened, but functional validation has not been done (Yang Z, An W, Liu S, et al. Mining of candidate genes involved in the biosynthesis of dextrorotatory borneol in *Cinnamomum burmannii* by transcriptomic analysis on three chemotypes[J]. PeerJ, 2020, 8(4): e9311.).

The existing reports have not found the relevant gene cloning and functional validation studies of the key enzymes in the biosynthetic pathway of borneol in the physiological type of *Cinnamomum burmannii*.

SUMMARY OF THE INVENTION

The technical problem to be solved by the present invention is to obtain a new *Cinnamomum burmannii* monoterpene synthase which participates in the synthesis of monoterpenes, so as to synthesize or prepare dextrorotatory borneol.

In order to solve the above problem, the present invention provides a protein first, and the protein is CbTPS1, which is derived from physiological type of *Cinnamomum burmannii*, named as *Cinnamomum burmannii* monoterpene synthase CbTPS1, being a protein of a), b), or c) as follows:

a) a protein having the amino acid sequence shown in SEQ ID NO: 2;

b) a fusion protein obtained by linking tags at the N-terminus and/or the C-terminus of the protein shown in SEQ ID NO: 2;

c) a protein having the same function as the protein shown in SEQ ID NO: 2, which is obtained by performing substitution and/or deletion and/or addition of one or more amino acid residues on the amino acid sequence shown in SEQ ID NO: 2.

Among them, SEQ ID NO: 2 consists of 603 amino acid residues.

The above protein can be artificially synthesized or obtained by first synthesizing their encoding genes and then performing biological expression.

In the above protein, the protein-tag refers to a polypeptide or protein subjected to fusion expression with a target protein by using in-vitro DNA recombination technology, so as to facilitate expression, detection, tracing and/or purification of the target protein. The protein-tag can be a Flag tag, a His tag, a MBP tag, a HA tag, a myc tag, a GST tag and/or a SUMO tag.

In embodiments of the present invention, the fusion protein is a protein having the amino acid sequence shown in SEQ ID NO: 3.

In the above protein, the identity refers to an identity of amino acid sequences. The identity of amino acid sequences can be determined by using a homology search site on the international internet, such as the BLAST webpage of the NCBI homepage website. For example, in advanced BLAST2.1, by using blastp as the program, the Expect value is set to be 10, all Filters are set to be OFF, BLOSUM62 is used as Matrix, Gap existence cost, Per residue gap cost and Lambda ratio are respectively set to be 11, 1 and 0.85 (default values), an identity of a pair of amino acid sequences is searched for calculation, and then an identity value (%) can be obtained.

In the above protein, the at least 90% identity can be at least 91%, 92%, 95%, 96%, 98%, 99% or 100% identity.

The related biological material of CbTPS1 is also within the protection scope of the present invention.

The related biological material of CbTPS1 provided by the present invention is represented by any one of the following A1) to A12):

A1) a nucleic acid molecule encoding CbTPS1;

A2) an expression cassette containing the nucleic acid molecule of A1);

A3) a recombinant vector containing the nucleic acid molecule of A1);

A4) a recombinant vector containing the expression cassette of A2);

A5) a recombinant microorganism containing the nucleic acid molecule of A1);

A6) a recombinant microorganism containing the expression cassette of A2);

A7) a recombinant microorganism containing the recombinant vector of A3);

A8) a recombinant microorganism containing the recombinant vector of A4);

A9) a transgenic plant cell line containing the nucleic acid molecule of A1);

A10) a transgenic plant cell line containing the expression cassette of A2);

A11) a transgenic plant cell line containing the recombinant vector of A3);

A12) a transgenic plant cell line containing the recombinant vector of A4).

In the above biological material, the nucleic acid molecule of A1) is represented by any one of the following B1)-B5):

B1) a DNA molecule shown in SEQ ID NO: 1 in the sequence listing;

B2) a DNA molecule encoding the sequence shown in SEQ ID NO: 1 in the sequence listing;

B3) a DNA molecule shown in SEQ ID NO: 4 in the sequence listing;

B4) a DNA molecule encoding the sequence shown in SEQ ID NO: 4 in the sequence listing; and B5) a DNA molecule which is hybridized with the DNA molecule defined in B1) or B2) or B3) or B4) under a strict condition and encodes CbTPS1.

Among them, SEQ ID NO: 1 in the sequence listing consists of 1812 nucleotides, and encodes the protein shown in SEQ ID NO: 2.

The strict condition refers to performing hybridization at 68° C. in 2×SSC buffer with 0.1% SDS, and washing the membrane twice for 5 minutes each, and then performing hybridization at 68° C. in 0.5×SSC buffer with 0.1% SDS, and washing the membrane twice for 15 minutes each.

Among them, the nucleic acid molecule can be DNA, such as cDNA, genomic DNA or recombinant DNA, and the nucleic acid molecule can also be RNA, such as mRNA or hnRNA.

In the above biological material, the expression cassette containing the nucleic acid molecule encoding CbTPS1 of A2) (CbTPS1 gene expression cassette) refers to a DNA capable of expressing CbTPS1 in a host cell, and the DNA not only can comprise a promoter for promoting CbTPS1 transcription, but also can comprise a terminator for terminating CbTPS1 transcription. Further, the expression cassette can further comprise an enhancer sequence.

In the above biological material, the vector can be a plasmid, a cosmid, a phage or a virus vector.

In the above biological material, the microorganism can be a yeast, a bacterium, an alga or a fungus, such as *Agrobacterium tumefaciens*.

In the above biological material, all of the transgenic plant cell lines may or may not comprise propagation materials.

The present invention further provides use of the above protein or the above related biological material.

The use is specifically represented by the followings:

1) use of the above protein as a monoterpene synthase;

2) use of the above related biological material in preparing a monoterpene synthase;

3) use of the above protein or the above related biological material in preparing or synthesizing a monoterpene compound; and 4) use of the above protein or the above related biological material in catalyzing the formation of dextrorotatory borneol from geranyl pyrophosphate.

In the above use, the monoterpene compound is dextrorotatory borneol.

The present invention also provides a method for preparing CbTPS1.

In the present invention, the method for preparing CbTPS1 comprises the steps of: introducing the encoding gene of CbTPS1 into a recipient microorganism to obtain a recombinant microorganism expressing CbTPS1, and culturing the recombinant microorganism to express CbTPS1.

In the above method, the recipient microorganism is a prokaryotic microorganism. Specifically, the prokaryotic microorganism is *Escherichia coli*. More specifically, the *Escherichia coli* is the *Escherichia coli* Transetta (DE3).

In the above method, the encoding gene of CbTPS1 can be introduced into the *Escherichia coli* Transetta (DE3) through a recombinant plasmid pET32a::CbTPS1; and the recombinant plasmid pET32a::CbTPS1 is obtained by constructing the Cbtps1 gene shown in SEQ ID NO: 1 at the BamHI site of a pET32a(+) vector, and the rest sequence of the pET32a(+) vector remains unchanged.

The present invention further provides a method for preparing dextrorotatory borneol, which comprising the step of catalyzing geranyl pyrophosphate (GPP) with CbTPS1.

In the above method, it is also necessary to add an enzymatic buffer in the catalytic process, and the enzymatic buffer consists of HEPES, $MgCl_2$ and DTT;

the concentration of HEPES in the enzymatic buffer is 25 mM;

the concentration of $MgCl_2$ in the enzymatic buffer is 5 mM;

the concentration of DTT in the enzymatic buffer is 5 mM; and the pH of the enzymatic buffer is 7.0.

In the above method, the method further comprises the step of performing a dephosphorylation reaction on the obtained enzymatic reaction product after catalyzing geranyl pyrophosphate (GPP) with CbTPS1, to obtain dextrorotatory borneol.

The present invention further provides a method for biosynthesizing dextrorotatory borneol.

The method for biosynthesizing dextrorotatory borneol of the present invention comprises the steps of: introducing the encoding gene of CbTPS1 into *Saccharomyces cerevisiae* to obtain recombinant *Saccharomyces cerevisiae*, and fermenting the recombinant *Saccharomyces cerevisiae* to obtain dextrorotatory borneol.

In the above method, the yeast *Saccharomyces cerevisiae* is specifically BY-Mono.

In the above method, the encoding gene of CbTPS1 can be introduced into BY-Mono through a recombinant plasmid pESC-Leu::CbTPS1; and the recombinant plasmid pESC-Leu::CbTPS1 is obtained by constructing the Cbtps1 gene shown in SEQ ID NO: 1 at the BamHI site of a pESC-Leu vector, and the rest sequence of the pESC-Leu vector remains unchanged.

DETAILED DESCRIPTION OF THE INVENTION

Figure 1:
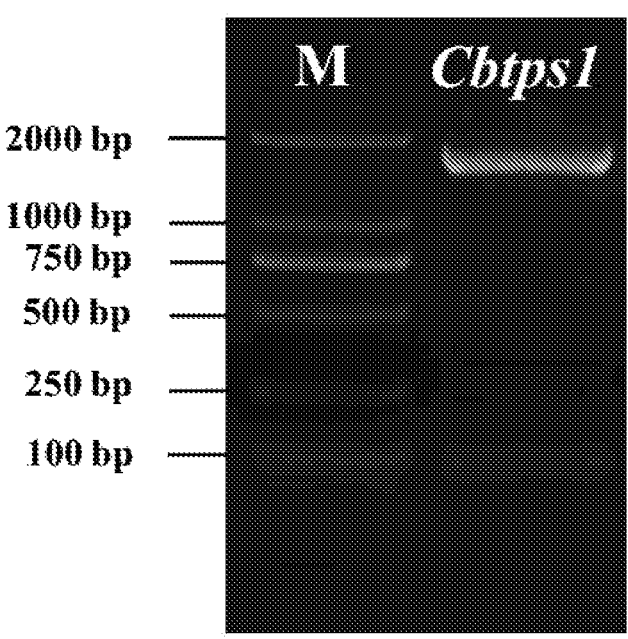
FIG. 1 is the agarose gel electrophoretogram of Cbtps1 gene of physiological type of *Cinnamomum burmannii*; M represents Trans2K DNA Marker (a nucleic acid molecular weight standard, with bands being 2000 bp, 1000 bp, 750 bp, 500 bp, 250 bp and 100 bp from top to bottom, respectively), and Cbtps1 represents Cbtps1 gene.

The following examples facilitate a better understanding of the present invention, but do not limit the present invention. The experimental methods in the following examples are all conventional methods unless otherwise specified. All the test materials used in the following examples are purchased from conventional biochemical reagent shops unless otherwise specified. The quantitative tests in the following examples are all set to repeat the experiments three times, and the results are averaged.

The Phusion® High-Fidelity DNA Polymerase and the restriction endonuclease BamHI in the following examples are products of New England Biolabs Company;

Quick RNA isolation kit is a product of Huayueyang Biotechnology (Beijing) Co., Ltd.;

TransScript One-Step gDNA Removal and cDNA Synthesis SuperMix, Trans2K DNA Marker, pEASY-Uni Seamless Cloning and Assembly Kit and *Escherichia coli* competent cell Transetta (DE3) are products of Beijing TransGen Biotech Co., Ltd.;

Premixed Protein Marker (Low) is a product of Takara Company;

PageRuler™ Prestained Protein Ladder is a product of ThermoFisher Scientific Company;

pET32a(+) vector is a product of Novagen Company;

Ni-NTA Agarose is a product of Qiagen Company (product catalog number: 30210);

Protein purification reagents and SDA-PAGE, $Na_2HPO_4$, NaCl, DTT, PMSF, Imidazole, and acrylamide/methylene bisacrylamide (30% solution) are products of Sangon Bioengineering (Shanghai) Co., Ltd.;

Protein ultrafiltration tube (Amicon-Ultra-15) is a product of Millipore Company (product catalog number: UFC903024);

pESC-Leu vector is a product of Agilent Company;

SD-Ura and SD-Ura-Leu are products of Beijing FunGenome Company;

ZYMO RESEARCH Frozen-EZ Yeast Transformation II kit is a product of Zymo Research Company;

BY4741 yeast strain (genotype: MATa his3Δ1 leu2Δ0 met15Δ0 ura3Δ0) is a product of Huayueyang Biotechnology (Beijing) Co., Ltd.;

Geranyl pyrophosphate (GPP) is a product of Sigma Company, with a product catalog number G6772 and a CAS number 763-10-0;

Dextrorotatory ((+)-borneol) is a product of Sigma Company, with a product catalog number CRM40901 and a CAS number 464-43-7.

Example 1. Full-Length cDNA Sequence Clone of CbTPS1 Gene of Physiological Type of *Cinnamomum burmannii*

1. Extraction of Total RNA

According to the instructions of the Quick RNA isolation kit of Huayueyang Biotechnology (Beijing) Co., Ltd., the total RNA from physiological type of *Cinnamomum burmannii* leaves was extracted.

2. Synthesis of First-Strand cDNA

According to the instructions of the first-strand cDNA synthesis kit TransScript One-Step gDNA Removal and cDNA Synthesis SuperMix of Beijing TransGen Biotech Co., Ltd., the cDNA was obtained by reverse transcription.

Wherein, the reverse transcription reaction system was as follows.

TABLE 1

| | |
|---|---|
| Total RNA | 5.0 μg |
| Anchored Oligo(dT)$_{18}$ Primer | 1.0 μL |
| 2 × TS Reaction Mix | 10.0 μL |
| TransScript ® RT/RI Enzyme Mix | 1.0 μL |
| gDNA Remover | 1.0 μL |
| RNase-free Water | added to a final volume of 20.0 μL |
| Total volume | 20.0 μL |

The steps of reverse transcription were as follows:

(1) in order to improve the synthesis efficiency, the Total RNA, Anchored Oligo(dT)$_{18}$ Primer and RNase-free Water were evenly mixed in a PCR tube at 65° C. for 5 minutes;

(2) 10.0 μL of 2×TS Reaction Mix, 1.0 μL of TransScript® RT/RI Enzyme Mix and 1.0 μL of gDNA Remover were added into the above PCR tube, and mixed evenly and gently;

(3) the reverse transcription reaction was performed at "42° C. for 30 minutes, 85° C. for 5 seconds" to obtain the first-strand cDNA;

(4) the first-strand cDNA was stored at −20° C.

3. Design of Primers

According to the transcriptome data of physiological type of *Cinnamomum burmannii* leaves, the open reading frame (ORF) sequence was obtained. Based on this, cloning primers CbTPS1-F1 and CbTPS1-R1 were designed. The sequences of the primers were as follows:

```
                                       (SEQ ID NO: 10)
    CbTPS1-F1: 5'-ATGGCGTTGCAAATGACTGTTCCA-3';

(SEQ ID NO: 11)
    CbTPS1-R1: 5'-TCAGGCATATCCACCATCGACACA-3'.
```

4. PCR Amplification

The PCR amplification was performed with high-fidelity enzyme Phusion® High-Fidelity DNA Polymerase, with the first-strand cDNA obtained in step 2 as template and CbTPS1-F1 and CbTPS1-R1 as primers. The results are shown in FIG. 1. The PCR amplification product was sequenced.

Wherein the PCR amplification procedure was as follows: pre-denaturation at 98° C. for 3 minutes; 35 cycles of (98° C. for 20 seconds, 55° C. for 20 seconds, 72° C. for 1 minute); and extension at 72° C. for 5 minutes.

Sequencing results show that: the sequence of the PCR amplification product is consistent with SEQ ID NO: 1, the gene shown in SEQ ID NO: 1 is named CbTPS1, which encodes a protein consisting of 603 amino acid residues, wherein the protein is named as CbTPS1 and the amino acid sequence of the protein is SEQ ID NO: 2.

Example 2. Acquisition and Functional Analysis of CbTPS1 of Physiological Type of *Cinnamomum burmannii*

I. Acquisition of CbTPS1 Protein of Physiological Type of *Cinnamomum burmannii*

1. Construction of Recombinant Vector

The CbTPS1 gene shown in SEQ ID NO: 1 was inserted at the BamHI restriction enzyme site of the pET32a(+) vector (Novagen Company) by using the pEASY-Uni Seamless Cloning and Assembly Kit of Beijing TransGen Biotech Co., Ltd., and the rest sequence of the pET32a(+) vector remains unchanged to obtain a recombinant plasmid pET32a::CbTPS1 (which has been verified by sequencing).

Specific steps were as follows:

1) the PCR amplification product obtained in Example 1 was used as a template, PCR amplification was performed with primers CbTPS1-F2 and CbTPS1-R2, the purified PCR product was obtained through recovering and purifying steps. The sequences of the primers were as follows (the underlined sequences were vector homologous regions):

```
CbTPS1-F2:
                                       (SEQ ID NO: 12)
5'-CCATGGCTGATATCGGAATGGCGTTGCAAATGACTGTTCCA-3';

CbTPS1-R2:
                                       (SEQ ID NO: 13)
5'-ACGGAGCTCGAATTCGGTCAGGCATATCCACCATCGACACA-3'.
```

2) The pET32a(+) vector (Novagen Company) was digested with the restriction endonuclease BamHI, and the linearized vector backbone was recovered.

3) According to the instructions of the pEASY-Uni Seamless Cloning and Assembly Kit of Beijing TransGen Biotech Co., Ltd., the purified PCR product obtained in step 1) was cloned into the linearized vector backbone in step 2) to obtain a recombinant plasmid pET32a:: CbTPS1.

The exogenously inserted DNA molecule is fused with part of the nucleotides on the vector backbone to form the fusion gene shown in SEQ ID NO: 4 of the sequence listing, which encodes the fusion protein shown in SEQ ID NO: 3 of the sequence listing.

2. Acquisition of Recombinant Bacteria

The recombinant plasmid pET32a::CbTPS1 was transformed into expression strain *Escherichia coli* Transetta (DE3) (purchased from Beijing TransGen Biotech Co., Ltd.) to obtain pET32a::CbTPS1 recombinant bacteria. Meanwhile, *E. coli* Transetta (DE3) was transformed with the pET32a(+) vector without the target gene and this recombinant bacteria was used as control bacteria.

3. Inducing the Expression of Recombinant Protein CbTPS1

The pET32a::CbTPS1 recombinant bacteria and the control bacteria were respectively inoculated into 2 mL LB liquid medium (containing 100 mg/L ampicillin), shaken and cultured overnight at 37° C. The next day, the cells were diluted in 200 mL LB liquid medium in a ratio of 1: 100, shaken and cultured at 37° C. until the OD$_{600}$ reached 0.6 to 0.8, and then shaken at 18° C. for 1 hour. IPTG was added to a final concentration of 0.5 mM, and the mixture was continuously cultured in a shaking table at 18° C. for 24 hours to induce the expression of the target protein. The bacterial solution was centrifuged at 8000 g for 5 minutes, the supernatant was discarded, the cells of pET32a::CbTPS1 recombinant bacteria and the control bacteria were collected, and stored at −80° C. for later use.

4. Extraction of Recombinant Protein CbTPS1

The proteins in the pET32a::CbTPS1 recombinant bacteria and the control bacteria were extracted.

Specific steps were as follows: the CbTPS1 recombinant bacteria and the control bacteria were resuspended with 5 mL pre-cooled HEPES buffer (25 mM HEPES, 5 M $MgCl_2$, 5 M DTT, pH 7.0), sonication (at 30% power for 5 seconds by an interval of 5 seconds, which lasted for 5 minutes and was repeated once) in ice bath, and centrifuged at 12,000 g and 4° C. for 30 minutes to obtain the supernatant (i.e., the protein solutions) of the pET32a::CbTPS1 recombinant bacteria and the control bacteria respectively.

Figure 2:
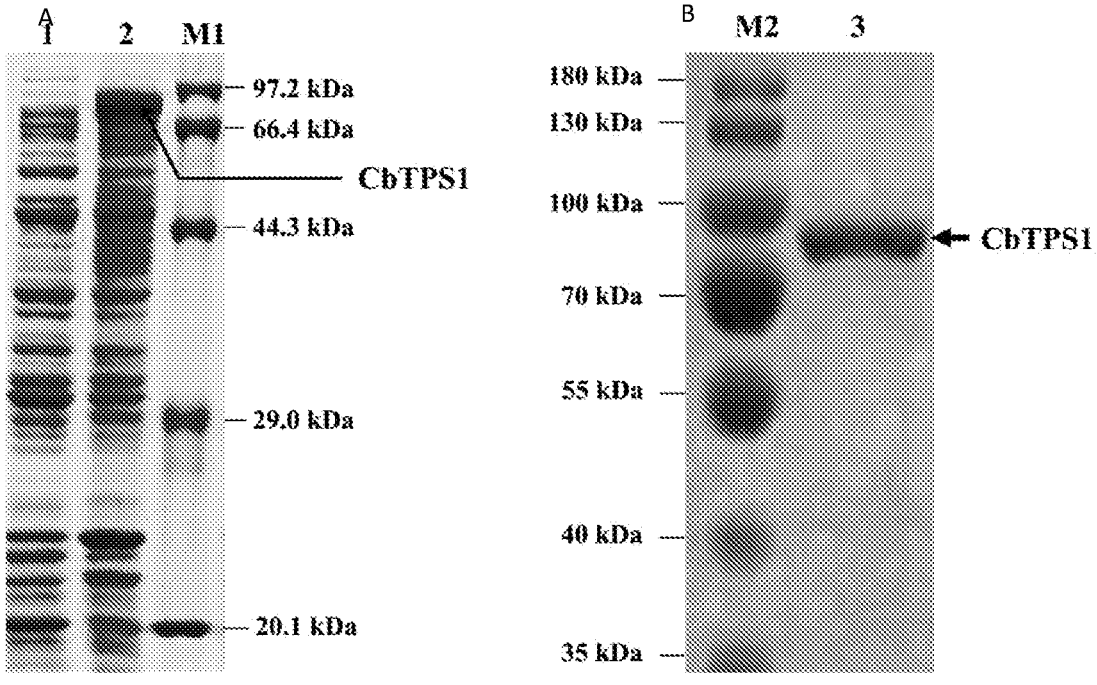
FIG. 2 shows the polyacrylamide gel electrophoresis (SDS-PAGE) analysis of CbTPS1 protein expressed in *Escherichia coli*. In panel A, M1 represents Premixed Protein Marker (Low) (a protein molecular weight standard, with bands being 97.2 KDa, 66.4 KDa, 44.3 KDa, 29.0 KDa and 20.1 KDa from top to bottom, respectively), lane 1 represents the electrophoresis result of the supernatant of the control bacteria, lane 2 represents the electrophoresis result of the supernatant of the pET32a::CbTPS1 recombinant bacteria; in panel B, M2 represents PageRuler™ Prestained Protein Ladder (a protein molecular weight standard, with bands being 180 KDa, 130 KDa, 100 KDa, 70 KDa, 55 KDa, 40 KDa and 35 KDa from top to bottom, respectively), lane 3 represents the electrophoresis result of the purified protein of the pET32a::CbTPS1 recombinant plasmid, and CbTPS1 with arrow represents the target protein expressed by the recombinant plasmid pET32a::CbTPS1 (i.e., the recombinant protein CbTPS1).

SDS-PAGE was performed on the supernatant of the pET32a::CbTPS1 recombinant bacteria and the supernatant of the control bacteria. The results are shown in FIG. 2A. It can be seen from the figure that the supernatant of the recombinant bacteria pET32a::CbTPS1 contains the recombinant protein CbTPS1, which is expressed by pET32a:: CbTPS1 recombinant plasmid, and the size of the recombinant protein CbTPS1 is about 88 kDa, which is consistent with the expected size. The supernatant of the control bacteria has no corresponding protein.

5. Purification of Recombinant Protein CbTPS1

Prepare reagents according to Table 2.

TABLE 2

| Preparation of protein eluents with different concentrations | | | | |
|---|---|---|---|---|
| | 0.2M $Na_2HPO_4$ (pH 7.4) | 3M NaCl | 1M imidazole | Ultra-pure water |
| Binding buffer (50 mL) | 5 mL | 8.33 mL | 0.5 mL | 36.17 mL |
| Elution buffer + 20 mM imidazole (50 mL) | 5 mL | 8.33 mL | 1 mL | 35.67 mL |
| Elution buffer + 50 mM imidazole (50 mL) | 5 mL | 8.33 mL | 2.5 mL | 34.17 mL |
| Elution buffer + 100 mM imidazole (50 mL) | 5 mL | 8.33 mL | 5 mL | 31.67 mL |
| Elution buffer + 250 mM imidazole (50 mL) | 5 mL | 8.33 mL | 12.5 mL | 24.17 mL |
| Elution buffer + 500 mM imidazole (50 mL) | 5 mL | 8.33 mL | 25 mL | 11.67 mL |

The specific purification process is as follows:

(1) the pET32a::CbTPS1 recombinant bacteria was resuspended with 5 mL pre-cooled Binding buffer (20 mM $Na_2HPO_4$, 0.5 mM NaCl, 10 mM imidazole, 1 mM DTT and 1 mM PMSF, pH 7.4);

(2) the bacteria solution was sonicated (at 30% power for 10 seconds by an interval of 10 seconds, which lasted for 20 minutes) in ice bath, and centrifuged at 12,000 g and 4° C. for 30 minutes;

(3) 200 μL Ni-NTA agorose was pipetted into a 15 mL centrifuge tube, washed with 10 times the volume of Elution buffer (containing 20 mM imidazole), and centrifuged at 500 g for 5 min at 4° C., then the supernatant was discarded (ethanol removed), and the nickel column was activated, repeated 3 times;

(4) the supernatant (crude protein) was mixed with the activated nickel column, and the centrifuge tube was placed horizontally on ice and shaken for 2 h to allow the protein fully bind to the nickel column;

(5) centrifuged at 500 g for 5 min at 4° C., then the supernatant was discarded;

(6) 5 mL Elution buffer (containing 20 mM imidazole) was added and resuspended gently, then centrifuged at 500 g for 5 min at 4° C., the supernatant was discarded, transferred to a 1.5 mL EP tube after repeating 3 times;

(7) 200 μL Elution buffer (containing 50 mM imidazole) was added, pipetted up and down to mix evenly, centrifuged at 500 g for 5 min at 4° C., then 50 μL of 50% glycerol was added into the supernatant (200 μL), and stored in refrigerator at −80° C.;

(8) 200 μL Elution buffer (containing 100 mM imidazole) was added, pipetted up and down to mix evenly, centrifuged at 500 g for 5 min at 4° C., then 50 μL of 50% glycerol was added into the supernatant (200 μL), and stored in refrigerator at −80° C.;

(9) 200 μL Elution buffer (containing 250 mM imidazole) was added, pipetted up and down to mix evenly, centrifuged at 500 g for 5 min at 4° C., then 50 μL of 50% glycerol was added into the supernatant (200 μL), and stored in refrigerator at −80° C.;

(10) 200 μL Elution buffer (containing 500 mM imidazole) was added, pipetted up and down to mix evenly, centrifuged at 500 g for 5 min at 4° C., then 50 μL of 50% glycerol was added into the supernatant (200 μL), and stored in refrigerator at −80° C.;

(11) the eluates with different concentration gradients were detected by SDS-PAGE protein electrophoresis, and the purified protein of pET32a::CbTPS1 was subjected to SDS-PAGE, the results are shown in FIG. 2B. It can be seen from the figure that the size of the recombinant protein CbTPS1 is about 88 kDa, which is consistent with the expected size, and the purification effect is good.

(12) the eluates containing the target protein were pooled together and transferred to a protein ultrafiltration tube for desalting concentration, and purified enzyme liquid was collected and stored in refrigerator at −80° C.

II. Enzymatic Activity Analysis of Recombinant Protein CbTPS1

1. Enzymatic Activity (1) An enzymatic reaction was performed with the supernatant of the pET32a::CbTPS1 recombinant bacteria, and to obtain an enzymatic reaction product. The specific steps of the enzymatic reaction were as follows: Enzyme assays were performed in 0.2 mL, including 190 μL of the supernatant of the pET32a:: CbTPS1 recombinant bacteria (the supernatant of the pET32a::CbTPS1 recombinant bacteria contained an enzymatic buffer, which was namely the HEPES buffer (25 mM HEPES, 5 M $MgCl_2$, 5 M DTT, pH 7.0)) and 10 μL geranyl pyrophosphate (GPP) as a substrate. After mixing evenly, the overall enzymatic reaction system was sealed with 200 μL of n-hexane covering solution and placed at 30° C. for 2 hours, then the n-hexane in the water phase was thoroughly removed under a stream of nitrogen (to avoid affecting the dephosphorylation reaction of the next step) to obtain an enzymatic reaction product of the supernatant of the pET32a::CbTPS1 recombinant bacteria.

(2) An enzymatic reaction was performed with the purified protein of pET32a::CbTPS1, and to obtain an enzymatic reaction product. The specific steps of the enzymatic reaction were as follows: The total enzymatic reaction system was 0.2 mL, including 20 μL the purified protein of pET32a::CbTPS1 (200 ng/L), 170 μL HEPES buffer (25 mM HEPES, 5 M $MgCl_2$, 5 M DTT, pH 7.0) and 10 μL geranyl pyrophosphate (GPP) as a substrate. After mixing evenly, the overall enzymatic reaction system was sealed with 200 μL n-hexane covering solution and placed at 30° C. for 2 hours, then the n-hexane in the water phase was thoroughly removed under a stream of nitrogen (to avoid affecting the dephosphorylation reaction of the next step) to obtain an enzymatic reaction product of the purified protein of pET32a::CbTPS1.

2. Dephosphorylation Reaction

A dephosphorylation reaction system was prepared, mixed fully (pipetted up and down), and dephosphorylated at 37° C. for 4 hours to obtain a dephosphorylated product.

The dephosphorylation reaction system is shown in Table 3.

TABLE 3

| | |
|---|---|
| Water phase (enzymatic reaction products of the supernatant of pET32a::CbTPS1 recombinant bacteria or the purified protein) | 200 μL |
| 10 × CutSmart Buffer | 22 μL |
| CIP | 2 μL |

The dephosphorylated product was extracted with n-hexane for three times, 0.2 mL each time, and the extracted organic phases were pooled together. The extracting solution was blow-dried with nitrogen, and added with 100 μL n-hexane for dissolution to obtain target compound (i.e., the target compound of the supernatant of the pET32a::CbTPS1 recombinant bacteria or the purified protein) for GC-MS analysis.

3. GC-MS Analysis

Gas chromatography-mass spectrometry GC-MS was used to detect the target compounds of the supernatant of the pET32a::CbTPS1 recombinant bacteria and the purified protein: the GC-MS analysis system was Thermo TRACE 1310/TSQ 8000 gas chromatograph, with an injection volume of 1 μL, a mode of splitless, a gas chromatographic column of Agilent J&W Cyclodex-B chiral column (30 mx 0.25 mmx 0.25 m) was used. And helium was used as carrier gas with flow rate of 1.0 mL/min. The injection port temperature was 220° C. and ion source temperature of 200° C., a heating program was following: 50° C. for 2 minutes, ramp up at a rate of 3° C.-min$^{-1}$ to 150° C., and hold 150° C. for 5 minutes, followed with a ramp up at a rate of 10° C.-min$^{-1}$ to 200° C. Ionization energy was set at 70 eV, and the sample was scanned in a range of 50 m/z to 500 m/z.

190 μL of the supernatant of the pET32a::CbTPS1 recombinant bacteria in the above reaction was replaced by 190 μL of the supernatant of the control bacteria, and the above experiment was repeated to obtain the target compound of the supernatant of the control bacteria.

Figure 3:
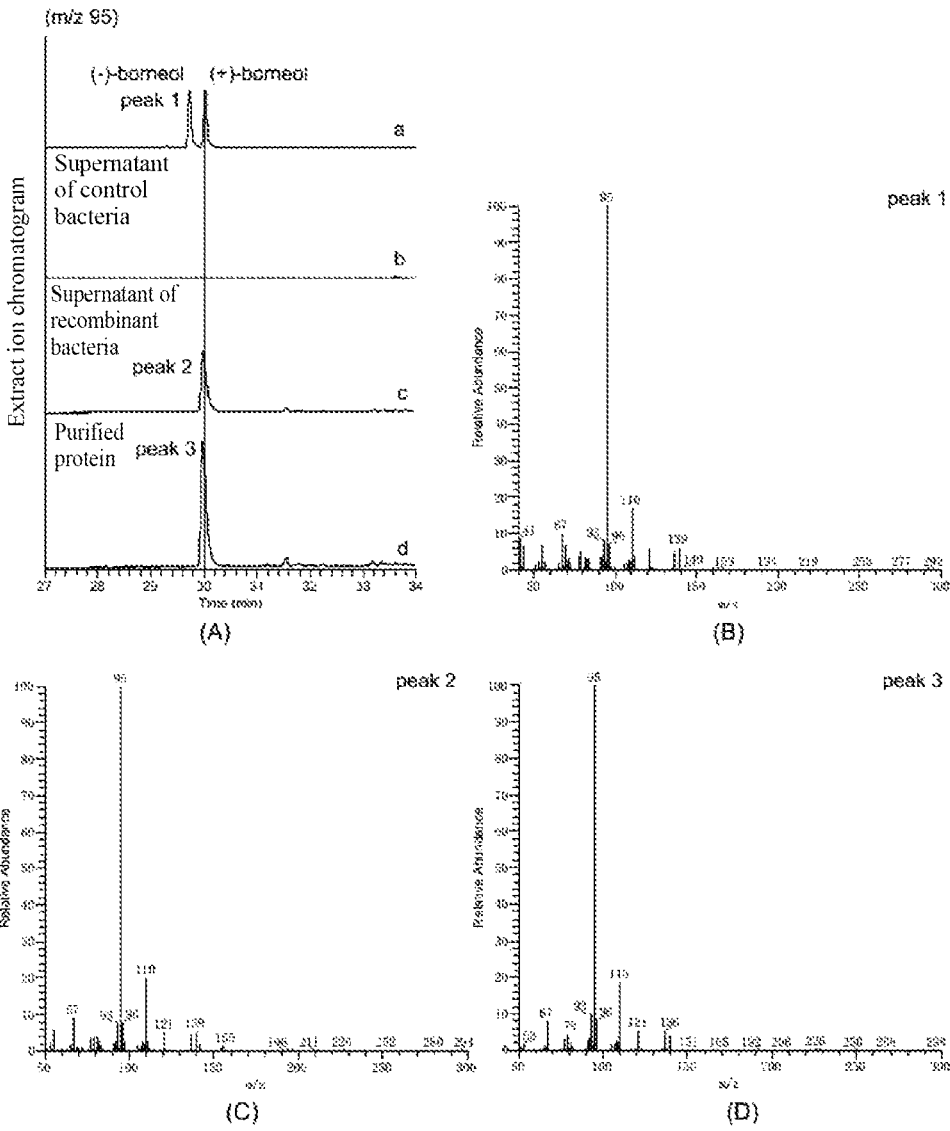
FIG. 3 shows the GC-MS analysis of the enzymatic reaction product of CbTPS1, wherein, in panel A, "a" represents the extract ion chromatogram of standard (−)-borneol and standard (+)-borneol, "b" represents the extract ion chromatogram of the target compound in the supernatant of the control bacteria, "c" represents the extract ion chromatogram of the target compound in the supernatant of the pET32a::CbTPS1 recombinant bacteria, and "d" represents the extract ion chromatogram of the target compound in the purified protein of pET32a::CbTPS1; panel B represents the mass spectrum of standard (+)-borneol; panel C represents the mass spectrum of the target compound in the supernatant of the pET32a::CbTPS1 recombinant bacteria; and panel D represents the mass spectrum of the target compound in the purified protein of pET32a::CbTPS1.

The results of the GC-MS analysis are shown in FIG. 3: dextrorotatory borneol ((+)-borneol) was not detected in the target compound of the supernatant of the control bacteria, but was detected in the target compounds of the supernatant of the pET32a::CbTPS1 recombinant bacteria and the purified protein, indicating that the recombinant protein CbTPS1 can catalyze the formation of dextrorotatory borneol ((+)-borneol) from GPP, and the recombinant protein CbTPS1 is a monoterpene synthase.

Example 3. Introduction of *Cinnamomum burmannii* CbTPS1 into Yeast Strain for Fermenting and Producing (+)-Borneol 1. Construction of Eukaryotic Expression Vector The Cbtps1 gene was inserted at the BamHI restriction enzyme site of the pESC-Leu vector (Agilent Company) by using the pEASY-Uni Seamless Cloning and Assembly Kit of Beijing TransGen Biotech Co., Ltd., and the rest sequence of the pESC-Leu vector remains unchanged to obtain a recombinant plasmid pESC-Leu::CbTPS1 (which has been verified by sequencing).

Specific steps were as follows:

1) the PCR amplification product obtained in Example 1 was used as a template, PCR amplification was performed with primers CbTPS1-F3 and CbTPS1-R3, and the purified PCR product was obtained through recovering and purifying steps. Wherein, the sequences of the primers were as follows (the underlined sequences were vector homologous regions): the sequences of the primers were as follows (the underlined sequences were vector homologous regions): CbTPS1-F3:

```
CbTPS1-F3:
                                (SEQ ID NO: 14)
5'-CCATGGCTGATATCGGAATGGCGTTGCAAATGACTGTTCCA-3';

CbTPS1-R3:
                                (SEQ ID NO: 15)
5'-ACGGAGCTCGAATTCGGTCAGGCATATCCACCATCGACACA-3'.
```

2) The pESC-Leu vector (Agilent Company) was digested with the restriction endonuclease BamHI, and then the linearized vector backbone was recovered.

3) According to the instructions of the pEASY-Uni Seamless Cloning and Assembly Kit of Beijing TransGen Biotech Co., Ltd., the purified PCR product obtained in step 1) was cloned into the linearized vector backbone in step 2) to obtain a recombinant plasmid pESC-Leu:: CbTPS1.

2. Construction of BY-Mono Yeast Strain

YPD solid medium: 1% of yeast extract+2% of peptone+ 2% of glucose+1.5% of agar; the corresponding liquid medium (YPD liquid medium) was prepared without adding the agar;

YPL induction medium: 1% of yeast extract+2% of peptone+2% of galactose; SD-Ura solid medium: SD-Ura+2% of glucose+2% of agar; the corresponding liquid medium (SD-Ura liquid medium) was prepared without adding the agar;

SD-Ura-Leu solid medium: SD-Ura-Leu+2% of glucose+ 2% of agar; the corresponding liquid medium (SD-Ura-Leu liquid medium) was prepared without adding the agar.

BY4741 yeast strain (genotype: MATa his3Δ1 leu2Δ0 met15Δ0 ura3Δ0) was coated on the YPD solid plate, and cultured upside down at 30° C. for 48 hours to 72 hours to obtain a newly activated BY4741 yeast colony. Ura3 marker, yeast-derived tHMGR1 (containing promoter sequence $P_{TDH3}$ and terminator sequence $T_{TPH}$, i.e., $P_{TDH3}$-tHMGR1-$T_{TPH}$), yeast-derived IDI1 (containing promoter sequence $P_{ADH1}$ and terminator sequence $T_{PGI}$, i.e., $P_{ADH1}$-IDI1-$T_{PGI}$), yeast-derived tHMGR1 (containing promoter sequence $P_{PGK1}$ and terminator sequence $T_{ADH1}$, i.e., $P_{PGK1}$-tHMGR1-$T_{ADH1}$), and yeast-derived ERG20$^{F96W-N127W}$ (containing promoter sequence $P_{TEF2}$ and terminator sequence $T_{CYC1}$, i.e., $P_{TEF2}$-ERG20$^{F96W\text{-}N127W}$-$T_{CYC1}$) were integrated at the YPRCΔ15 site (chromosome XVI long_terminal_repeat and Autonomously Replicating Sequence, YPRCΔ15) of the BY4741 yeast strain. Specific steps were as follows:

1) a fresh BY4741 yeast single colony was inoculated into 5 ml YPD liquid medium, cultured at 30° C. and shaken at 200 rpm until OD$_{600}$ of 0.6 to 1.0;

2) a cuvette (0.2 cm) soaked in ethanol was taken and then cleaned with ultra-pure water and air-dried, put upside down on filter paper, and finally placed in an ultra-clean table for sterilization;

3) 1 mL to 2 mL solution was added into a 1.5 mL sterile EP tube, centrifuged at 10,000 g for 1 minute at room temperature, and the supernatant was discarded;

4) 1 ml of pre-cooled sterile water was added for resuspending, then the resuspended cell solution was centrifuged at 10,000 g for 1 minute at room temperature;

5) repeated step 4) and then the supernatant was discarded, 1 mL of pre-cooled buffer (10 mM LiAc, 10 mM DTT, 0.6 M sorbitol, and 10 mM Tris-HCl (pH 7.5)) was added to the pelleted cells, then cultured at 25° C. for 20 minutes;

6) centrifuged at 10,000 g for 1 minute at room temperature and the supernatant was discarded;

7) 1 mL of pre-cooled sorbitol (1 M) solution was added to the pelleted cells for resuspending, then the resuspended cell solution was centrifuged at 10,000 g for 1 minute at room temperature;

8) repeated step 7) and then the supernatant was discarded. Resuspend in 100 μL pre-cooled sorbitol (1 M), and then BY4741 yeast competent cells were prepared;

9) five DNA fragments of Ura3 marker (SEQ ID NO: 5 of the sequence listing), $P_{TDH3}$-tHMGR1-$T_{TPH}$ (SEQ ID NO: 6 of the sequence listing), $P_{ADH1}$-IDI1-$T_{PGI}$ (SEQ ID NO: 7 of the sequence listing), $P_{PGK1}$-tHMGR1-$T_{ADH1}$ (SEQ ID NO: 8 of the sequence listing) and $P_{TEF2}$-ERG20$^{F96W\text{-}N127W}$-$T_{CYC1}$ (SEQ ID NO: 9 of the sequence listing) were mixed in equal molar ratio, with a total mass of 500 ng (the total volume was no more than 1/10 of the volume of the competent cells). The mixture of the above DNA fragments was added into the BY4741 yeast competent cells, mixed and transferred to a cuvette (0.2 cm), and incubated on ice for 2 minutes to 5 minutes; electrotransformation was performed under 2.7 kV, 25 F and 200Ω (Bio-Rad, Hercules, CA), and after electric shock, 1 mL of sorbitol (1 M) solution was added in an ultra-clean working table, then transferred into a 1.5 mL sterile EP tube, cultured at 30° C. for 1 to 2 hours, and mixed up and down for 2 to 3 times;

10) the mixture was centrifuged at 10,000 g for 1 minute at room temperature, the supernatant was discarded, and the pelleted cells were resuspended with the remaining 100 μL of solution. The resuspended cell solution was dropwise added in the center of the plate with synthetic dropout medium SD-Ura solid medium. The plate was evenly coated by using a coater until all the coated cell solution was completely absorbed, and placed upside down in an incubator at 30° C. and cultured for 2 to 3 days. The obtained strain was named as BY-Mono yeast strain, and the genotype of BY-Mono yeast was MATa his3Δ1 leu2Δ0 met15Δ0 ura3Δ0, YPRCΔ15 Ura3-$P_{TDH3}$-tHMGR1-$T_{TPH}$- $P_{ADH1}$-IDI1-$T_{PGI}$-$P_{PGK1}$-tHMGR1-$T_{ADH1}$-$P_{TEF2}$-ERG20$^{F96W\text{-}N127W}$-$T_{CYC1}$.

3. Preparation of BY-Mono Yeast Competent Cells

Yeast competent cells were prepared by using the ZYMO RESEARCH Frozen-EZ Yeast Transformation II kit:

(1) a fresh BY-Mono yeast colony was picked from the plate with SD-Ura solid medium, and inoculated into 10 mL of SD-Ura liquid medium, then shaken and cultured at 30° C. until OD$_{600}$ of 0.8 to 1.0;

(2) centrifuged at 500 g for 4 minutes at room temperature, and the supernatant was discarded;

(3) 10 mL Frozen-EZ Solution 1 was added to suspend the pelleted cells, and the suspended cell solution was centrifuged at 500 g for 4 minutes at room temperature, and the supernatant was discarded;

(4) 1 mL Frozen-EZ Solution 2 was added to suspend the pellet cells to obtain the BY-Mono yeast competent cells, and the BY-Mono yeast competent cells were sub-packaged into 1.5 mL sterile EP tubes, with 50 μL in each tube;

(5) BY-Mono competent cells were slowly cooled to −70° C. (4° C. for 1 hour; −20° C. for 1 hour; −40° C. for 1 hour; stored at −70° C.), and it was forbidden to quick freeze the competent cells with liquid nitrogen.

4. Transformation of Recombinant Plasmid pESC-Leu:: CbTPS1 into BY-Mono Competent Cells (1) 0.2-1 g recombinant plasmid pESC-Leu::CbTPS1 (in less than 5 μL) with 50 μL of BY-Mono yeast competent cells were mixed;

(2) 500 μL Frozen-EZ Solution 3 was added and mixed thoroughly;

(3) incubated at 30° C. for 1 to 2 hours, and mixed for 2 to 3 times during this period;

(4) 50-150 μL the above incubated cell solution was coated on the plate with SD-Ura-Leu solid medium, air-dried, and then invertedly incubated at 30° C. for 48 to 96 hours to obtain a recombinant yeast transformed with the recombinant plasmid pESC-Leu::CbTPS1, which was named as BY-Mono/pESC-Leu::CbTPS1.

Meanwhile, the pESC-Leu vector without the target gene (i.e., the Cbtps1 gene) was transformed into the BY-Mono yeast competent cells by the same method as above and used as a control, to obtain a recombinant yeast transformed with the pESC-Leu vector, which was named as BY-Mono/pESC-Leu.

5. Fermentation (1) The BY-Mono/pESC-Leu::CbTPS1 single colony grown on the plate with SD-Ura-Leu solid medium in step 4 was picked, and inoculated into 10 mL of SD-Ura-Leu liquid medium at 200 rpm and 30° C. for 48 hours.

(2) the cells were harvested and centrifuged at 5,000 g for 5 minutes at room temperature, then the cells were transferred into 20 mL of YPL induction medium, and cultured at 200 rpm and 30° C. for 72 hours to obtain a fermentation product.

6. Extraction of Fermentation Product

The target compound was terpenoid, which was fat-soluble and easily soluble in ethyl acetate. Therefore, ethyl acetate was selected as a solvent to extract the fermentation product, to obtain the target compound. Wherein, the steps of the extraction were as follows:

(1) the fermented solution was collected, which was the fermentation product, and added with an equal volume of ethyl acetate;

(2) the above mixture was sonicated for 1 hour, and shaken and mixed for many times during this period;

(3) the upper organic phase was taken and centrifuged at 5,000 g for 5 minutes at room temperature, and an appropriate amount of anhydrous sodium sulfate (dried at 120° C. for 30 minute) was added, and shaken during addition to remove the water in the extract;

(4) the solution was concentrated on a rotary evaporator to be nearly dry;

(5) the concentrated solution was pipetted, and filtered through a 0.22 m PTFE needle filter, and the filtrate was stored in vial, sealed with a sealing film, and stored in a refrigerator at 4° C.

7. GC-MS Detection of Fermentation Product

Gas chromatography-mass spectrometry GC-MS was used to detect the target compound: the GC-MS analysis system was Thermo TRACE 1310/TSQ 8000 gas chromatograph, with an injection volume of 1 μL, a mode of splitless. A gas chromatographic column of Thermo Scientific TG-5MS (30 m×0.25 mm×0.25 μm) was used. And helium was used as carrier gas with flow rate of 1.0 mL/min. The injection port temperature was 220° C. and ion source temperature of 200° C., a heating program was following: hold at 50° C. for 2 minutes, increased from 50° C. to 150° C. by 5° C. min$^{-1}$ and hold 150° C. for 2 minutes, then increased to 300° C. by 30° C. min$^{-1}$. Ionization energy was set at 70 eV, and the sample was scanned in a range of 50 m/z to 500 m/z.

In the fermentation of the above step 5, "the BY-Mono/pESC-Leu::CbTPS1 single colony grown on the plate with SD-Ura-Leu solid medium in step 4 was picked" was replaced by "the BY-Mono/pESC-Leu single colony grown on the plate with SD-Ura-Leu solid medium in step 4 was picked", and the above experiment steps 5, 6 and 7 were repeated.

Figure 4:
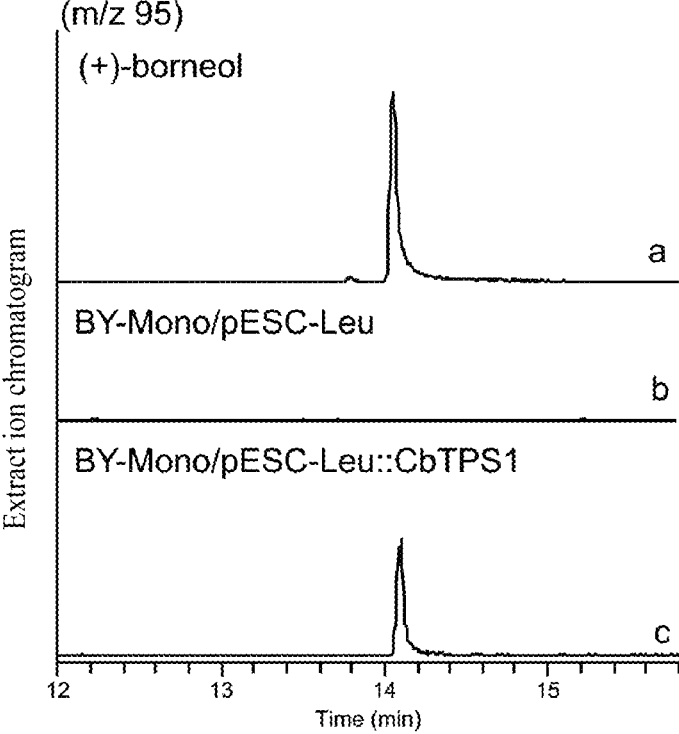
FIG. 4 shows the GC-MS analysis of (+)-borneol fermented and produced by introducing CbTPS1 into yeast strain (BY-Mono); wherein "a" represents the extract ion chromatogram of standard (+)-borneol, "b" represents the extract ion chromatogram of the target compound obtained by extracting the fermentation product of the recombinant yeast strain BY-Mono/pESC-Leu, and "c" represents the extract ion chromatogram of the target compound obtained by extracting the fermentation product of the recombinant yeast strain BY-Mono/pESC-Leu::CbTPS1.

The results of GC-MS analysis are shown in FIG. 4: the target compound obtained by extracting the fermentation product of the recombinant yeast strain BY-Mono/pESC-Leu::CbTPS1 which contains the recombinant plasmid pESC-Leu::CbTPS1 is dextrorotatory borneol, i.e., dextrorotatory borneol ((+)-borneol) can be synthesized by the recombinant yeast strain BY-Mono/pESC-Leu::CbTPS1 which contains the recombinant plasmid pESC-Leu:: CbTPS1, and about 3.0 mg of dextrorotatory borneol can be obtained from per liter of fermentation broth through statistics. Dextrorotatory borneol ((+)-borneol) is not detected in the target compound obtained by extracting the fermentation product of the recombinant yeast strain BY-Mono/pESC-Leu which contains the pESC-Leu vector.

The present invention is described in detail above. For those skilled in the art, the present invention can be implemented in a wide range under equivalent parameters, concentrations and conditions without departing from the purpose and scope of the present invention and unnecessary experiments. Although the present invention gives specific examples, it should be understood that the present invention can be further improved. In a word, according to the principle of the present invention, the present application is intended to comprise any changes, uses or improvements of the present invention, comprising changes that deviate from the scope disclosed in the present application but are made by conventional techniques known in the art. According to the scope of the following appended claims, some basic features can be applied.

INDUSTRIAL APPLICATION

The Cbtps1 gene is cloned from the cDNA of physiological type of *Cinnamomum burmannii* in the present invention, and the gene is a key enzyme gene for the synthesis of a monoterpene ingredient obtained from physiological type of *Cinnamomum burmannii* for the first time. It has been proven by experiments that: the CbTPS1 protein of the present invention can catalyze the formation of dextrorotatory borneol ((+)-borneol) from GPP, and has an important role in the biosynthesis of dextrorotatory borneol and other monoterpene compounds in physiological type of *Cinnamomum burmannii*, and provides an important basis for increasing the content of the active ingredient dextrorotatory borneol in physiological type of *Cinnamomum burmannii* by using a genetic engineering technology or directly producing dextrorotatory borneol, thus further having important theoretical and practical significances for regulating and producing plant monoterpene compounds and culturing high-quality physiological type of *Cinnamomum burmannii*.

40

The invention claimed is:

1. A fusion protein, wherein the sequence of the fusion protein is shown in SEQ ID NO: 3.

2. A method for preparing the fusion protein according to claim 1, wherein the method comprises the steps of: introducing a nucleotide sequence encoding the fusion protein according to claim 1 into a recipient microorganism to obtain a recombinant microorganism expressing the fusion protein according to claim 1, and culturing the recombinant microorganism to express the fusion protein according to claim 1.

3. A method for biosynthesizing dextrorotatory borneol, wherein the method comprises the steps of: introducing the encoding gene of the fusion protein according to claim 1 into *Saccharomyces cerevisiae* to obtain recombinant *Saccharomyces cerevisiae*, and fermenting the recombinant *Saccharomyces cerevisiae* to obtain the dextrorotatory borneol.

4. A method for preparing or synthesizing a monoterpene compound, wherein the method comprises the step of using the fusion protein according to claim 1 to prepare or synthesize the monoterpene compound.

5. A method for catalyzing the formation of dextrorotatory borneol from geranyl pyrophosphate, wherein the method comprises the step of catalyzing the formation of dextrorotatory borneol from geranyl pyrophosphate with the fusion protein according to claim 1.

* * * * *